(12) United States Patent
Sekowski et al.

(10) Patent No.: US 11,103,127 B2
(45) Date of Patent: Aug. 31, 2021

(54) STEERABLE MICRO-ENDOSCOPE

(71) Applicant: RESEARCH DEVELOPMENT INTERNATIONAL CORPORATION, Pasadena, CA (US)

(72) Inventors: Marek Sekowski, Pacific Palisades, CA (US); Russ Meek, Sierra Madre, CA (US)

(73) Assignee: RESEARCH DEVELOPMENT INTERNATIONAL CORPORATION, Pasadena, CA (US)

( * ) Notice: Subject to any disclaimer, the term of this patent is extended or adjusted under 35 U.S.C. 154(b) by 909 days.

(21) Appl. No.: 15/751,153

(22) PCT Filed: Apr. 22, 2015

(86) PCT No.: PCT/US2015/027170
§ 371 (c)(1),
(2) Date: Feb. 7, 2018

(87) PCT Pub. No.: WO2016/064449
PCT Pub. Date: Apr. 28, 2016

(65) Prior Publication Data
US 2018/0228346 A1  Aug. 16, 2018

Related U.S. Application Data

(60) Provisional application No. 62/066,340, filed on Oct. 20, 2014.

(51) Int. Cl.
*A61B 1/005* (2006.01)
*A61B 1/05* (2006.01)
(Continued)

(52) U.S. Cl.
CPC .......... *A61B 1/0052* (2013.01); *A61B 1/0055* (2013.01); *A61B 1/0057* (2013.01);
(Continued)

(58) Field of Classification Search
CPC ... A61B 1/0052; A61B 1/0055; A61B 1/0057; A61B 1/00087
See application file for complete search history.

(56) References Cited

U.S. PATENT DOCUMENTS

| | | |
|---|---|---|
| 4,398,910 A | 8/1983 | Blake |
| 4,402,685 A | 9/1983 | Buhler |
(Continued)

FOREIGN PATENT DOCUMENTS

| | | |
|---|---|---|
| CN | 1861010 A | 11/2006 |
| CN | 102438532 A | 5/2012 |
(Continued)

OTHER PUBLICATIONS

International Search Report for PCT/CN2015/095780, dated Jul. 27, 2015.
(Continued)

*Primary Examiner* — Timothy J Neal
*Assistant Examiner* — Jae Woo
(74) *Attorney, Agent, or Firm* — Ladas & Parry, LLP

(57) ABSTRACT

A steerable micro-device comprising a cylindrical elongated member having a distal end and a proximal end, the elongated member comprising at least a first lumen, a tensioning wire running in the first lumen, a distal end of the tensioning wire being attached at the distal end of the elongated member and a proximal end of the tensioning wire exiting the first lumen at the proximal end of the elongated member; the elongated member having a proximal portion extending from the proximal end toward the distal end of the elongated member and a distal portion extending from the distal end to the proximal portion of the elongated member, the proximal portion having a first durometer and the distal portion having a second durometer, lower than the first durometer the first lumen being arranged such that the distal portion of the
(Continued)

elongated body bends when the proximal end of the tensioning wire is pulled.

19 Claims, 21 Drawing Sheets

(51) Int. Cl.
| | |
|---|---|
| *A61B 1/00* | (2006.01) |
| *G02B 23/24* | (2006.01) |
| *A61B 1/018* | (2006.01) |
| *A61B 18/14* | (2006.01) |
| *A61B 17/00* | (2006.01) |

(52) U.S. Cl.
CPC ............ *A61B 1/05* (2013.01); *G02B 23/2476* (2013.01); *A61B 1/00087* (2013.01); *A61B 1/018* (2013.01); *A61B 18/1492* (2013.01); *A61B 2017/00318* (2013.01)

(56) References Cited

U.S. PATENT DOCUMENTS

| | | | |
|---|---|---|---|
| 4,451,256 A | 5/1984 | Weikl | |
| 4,498,902 A | 2/1985 | Ash | |
| 4,566,400 A * | 1/1986 | Keenan | G10K 1/072 |
| | | | 116/149 |
| 4,569,347 A | 2/1986 | Frisbie | |
| 4,580,551 A | 4/1986 | Siegmund | |
| 4,718,407 A * | 1/1988 | Chikama | A61B 1/0052 |
| | | | 138/118 |
| 4,781,690 A | 11/1988 | Ishida | |
| 4,788,967 A | 12/1988 | Ueda | |
| 4,798,193 A | 1/1989 | Giesy | |
| 4,888,000 A | 12/1989 | McQuilkin | |
| 4,997,424 A | 3/1991 | Little | |
| 5,147,332 A * | 9/1992 | Moorehead | A61M 25/0075 |
| | | | 604/247 |
| 5,195,978 A | 3/1993 | Schiffer | |
| 5,197,457 A | 3/1993 | Adair | |
| 5,299,562 A * | 4/1994 | Heckele | G02B 23/2423 |
| | | | 600/140 |
| 5,324,269 A | 6/1994 | Miraki | |
| 5,325,845 A | 7/1994 | Adair | |
| 5,342,299 A | 8/1994 | Snoke | |
| 5,383,852 A * | 1/1995 | Stevens-Wright | |
| | | | A61M 25/0136 |
| | | | 604/95.04 |
| 5,397,311 A | 3/1995 | Walker | |
| 5,405,334 A | 4/1995 | Roth | |
| 5,507,725 A * | 4/1996 | Savage | A61M 25/0144 |
| | | | 604/95.04 |
| 5,533,986 A | 7/1996 | Mottola | |
| 5,571,085 A * | 11/1996 | Accisano, III | A61M 25/0136 |
| | | | 604/95.01 |
| 5,704,899 A * | 1/1998 | Milo | A61B 1/0056 |
| | | | 600/161 |
| 5,817,072 A | 10/1998 | Lampropoulos | |
| 5,836,306 A | 11/1998 | Duane | |
| 6,030,360 A * | 2/2000 | Biggs | A61M 25/0136 |
| | | | 600/139 |
| 6,083,152 A * | 7/2000 | Strong | A61B 1/0055 |
| | | | 600/121 |
| 6,159,198 A | 12/2000 | Gardeski | |
| 6,171,235 B1 | 1/2001 | Konstorum | |
| 6,193,691 B1 | 2/2001 | Beardsley | |
| 6,497,681 B1 | 12/2002 | Brenner | |
| 6,740,030 B2 | 5/2004 | Martone | |
| 6,887,417 B1 | 5/2005 | Gawreluk | |
| 7,033,317 B2 | 4/2006 | Pruitt | |
| 7,048,719 B1 | 5/2006 | Monetti | |
| 7,658,738 B2 | 2/2010 | Nobis | |
| 8,029,473 B2 | 10/2011 | Carter | |
| 8,262,563 B2 | 9/2012 | Bakos | |
| 8,320,650 B2 | 11/2012 | Demos | |
| 8,517,921 B2 | 8/2013 | Tremaglio | |
| 8,932,208 B2 | 1/2015 | Kendale | |
| 9,468,362 B2 | 10/2016 | Goldfarb | |
| 10,368,910 B2 | 8/2019 | Eversull | |
| 2002/0068912 A1 | 6/2002 | Merdan | |
| 2002/0072712 A1 | 6/2002 | Nool | |
| 2003/0032941 A1 | 2/2003 | Boyle | |
| 2003/0093085 A1 | 5/2003 | Leopold | |
| 2003/0130564 A1 | 7/2003 | Martone | |
| 2003/0130620 A1 | 7/2003 | Alokaili | |
| 2003/0171650 A1 | 9/2003 | Tartaglia | |
| 2003/0187427 A1 * | 10/2003 | Gatto | A61B 1/043 |
| | | | 606/15 |
| 2003/0212373 A1 | 11/2003 | Hall | |
| 2003/0233024 A1 | 12/2003 | Ando | |
| 2003/0233115 A1 | 12/2003 | Eversull | |
| 2004/0059277 A1 | 3/2004 | Maguire | |
| 2004/0064147 A1 | 4/2004 | Struble | |
| 2004/0106852 A1 | 6/2004 | Windheuser | |
| 2005/0059890 A1 * | 3/2005 | Deal | A61B 1/018 |
| | | | 600/433 |
| 2005/0085841 A1 | 4/2005 | Eversull | |
| 2005/0107738 A1 | 5/2005 | Slater | |
| 2005/0124918 A1 | 6/2005 | Griffin | |
| 2005/0131279 A1 | 6/2005 | Boulais | |
| 2005/0149097 A1 | 7/2005 | Regnell | |
| 2005/0154262 A1 * | 7/2005 | Banik | A61B 1/00059 |
| | | | 600/179 |
| 2005/0182387 A1 | 8/2005 | Webler | |
| 2005/0222558 A1 * | 10/2005 | Baxter | A61B 18/1492 |
| | | | 606/16 |
| 2005/0256508 A1 | 11/2005 | Hall | |
| 2005/0261554 A1 * | 11/2005 | Scholly | A61B 1/00165 |
| | | | 600/160 |
| 2005/0261674 A1 * | 11/2005 | Nobis | A61B 1/00073 |
| | | | 606/45 |
| 2006/0030753 A1 | 2/2006 | Boutillette | |
| 2006/0030864 A1 | 2/2006 | Kennedy | |
| 2007/0043338 A1 | 2/2007 | Moll | |
| 2007/0215268 A1 | 9/2007 | Pingleton et al. | |
| 2007/0225559 A1 * | 9/2007 | Clerc | A61B 1/018 |
| | | | 600/117 |
| 2007/0249907 A1 | 10/2007 | Boulais | |
| 2007/0293726 A1 | 12/2007 | Goldfarb | |
| 2008/0015625 A1 | 1/2008 | Ventura | |
| 2008/0045787 A1 * | 2/2008 | Snay | A61B 1/00071 |
| | | | 600/109 |
| 2008/0132762 A1 | 6/2008 | Melville | |
| 2008/0154207 A1 | 6/2008 | Hardin | |
| 2008/0183035 A1 | 7/2008 | Vakharia | |
| 2008/0208133 A1 | 8/2008 | Lieberman | |
| 2008/0245371 A1 * | 10/2008 | Gruber | A61B 1/303 |
| | | | 128/831 |
| 2008/0262300 A1 * | 10/2008 | Ewers | A61B 1/00071 |
| | | | 600/114 |
| 2008/0319418 A1 | 12/2008 | Chong | |
| 2009/0049698 A1 | 2/2009 | Drake | |
| 2009/0171161 A1 | 7/2009 | Ewers | |
| 2009/0281376 A1 | 11/2009 | Acosta et al. | |
| 2010/0032470 A1 | 2/2010 | Hess | |
| 2010/0121269 A1 * | 5/2010 | Goldenberg | A61B 5/6885 |
| | | | 604/95.01 |
| 2010/0130850 A1 | 5/2010 | Pakter | |
| 2010/0145331 A1 | 6/2010 | Chrisitian | |
| 2010/0268123 A1 | 10/2010 | Callahan | |
| 2011/0245765 A1 * | 10/2011 | Jacobsen | A61B 1/05 |
| | | | 604/95.02 |
| 2012/0018082 A1 | 1/2012 | Kuboi | |
| 2012/0029421 A1 | 2/2012 | Drake | |
| 2012/0172663 A1 * | 7/2012 | Perretta | A61B 1/005 |
| | | | 600/106 |
| 2012/0184954 A1 | 7/2012 | Onishi | |
| 2012/0215071 A1 | 8/2012 | Mahlin | |
| 2012/0221007 A1 | 8/2012 | Batten et al. | |
| 2012/0296167 A1 * | 11/2012 | Chen | A61B 1/00073 |
| | | | 600/110 |

(56) References Cited

U.S. PATENT DOCUMENTS

| | | | | |
|---|---|---|---|---|
| 2013/0028554 | A1* | 1/2013 | Wong | A61B 5/065 385/12 |
| 2013/0046144 | A1 | 2/2013 | Iede | |
| 2013/0109919 | A1 | 5/2013 | Sugiyama | |
| 2013/0172673 | A1 | 7/2013 | Kennedy | |
| 2013/0253481 | A1 | 9/2013 | Dewaele | |
| 2013/0289352 | A1 | 10/2013 | Boulais | |
| 2014/0024951 | A1 | 1/2014 | Herzlinger | |
| 2014/0066706 | A1 | 3/2014 | McWeeney | |
| 2014/0073854 | A1 | 3/2014 | Vincent | |
| 2014/0135576 | A1 | 5/2014 | Hebert | |
| 2014/0148759 | A1 | 5/2014 | Mcnamara | |
| 2014/0243592 | A1 | 8/2014 | Kato | |
| 2014/0276966 | A1* | 9/2014 | Ranucci | A61M 25/0138 606/139 |
| 2016/0096004 | A1* | 4/2016 | Gerrans | A61M 25/0138 600/112 |
| 2016/0310701 | A1* | 10/2016 | Pai | A61M 25/0138 |
| 2017/0224956 | A1 | 8/2017 | Melsheimer | |
| 2017/0340193 | A1 | 11/2017 | Gambhir et al. | |
| 2018/0344987 | A1 | 12/2018 | Lancette | |
| 2019/0082940 | A1 | 3/2019 | Igov | |
| 2019/0117937 | A1* | 4/2019 | Humphrey | A61B 1/0052 |
| 2019/0224458 | A1 | 7/2019 | Morera | |
| 2019/0224459 | A1 | 7/2019 | Pedroni | |

FOREIGN PATENT DOCUMENTS

| | | |
|---|---|---|
| CN | 103654694 A | 3/2014 |
| CN | 107529958 A | 10/2014 |
| CN | 104219987 A | 12/2014 |
| JP | 2013-106713 A | 6/2013 |
| WO | 02/053221 | 7/2002 |
| WO | 2004-086957 | 10/2004 |
| WO | 2012-088167 A2 | 6/2012 |
| WO | 2016/064449 | 4/2016 |
| WO | 2016/064763 | 4/2016 |
| WO | 2016/171780 | 10/2016 |

OTHER PUBLICATIONS

Written Opinion of the International Search Authority for PCT/CN2015/095780, dated Jul. 27, 2015.
International Preliminary Report on Patentability Chapter 1 dated Apr. 25, 2017.
U.S. Appl. No. 15/751,150, Sekowski, filed Feb. 7, 2018.
PCT International Search Report from PCT/US2015/056279 dated Jan. 13, 2016.
PCT International Written Opinion from PCT/US2015/056279 dated Jan. 13, 2016.
PCT International Preliminary Report on Patentability (Chapter I) with Written Opinion from PCT/US2015/056279 dated Apr. 25, 2017.
PCT International Search Report from PCT/US2016/017033 dated May 10, 2016.
PCT International Written Opinion from PCT/US2016/017033 dated May 10, 2016.
PCT International Preliminary Report on Patentability (Chapter I) with Written Opinion from PCT/US2016/017033 dated Oct. 24, 2017.
EPO partial supplementary search report from European Patent Application No. 15852048.6 dated Mar. 7, 2018.
U.S. Appl. No. 16/332,762, Sekowski, filed Mar. 12, 2019.
Office action from Chinese Patent Application No. 201580068469.1 dated Sep. 29, 2018 with search report and its English translation.
Office action from Chinese Patent Application No. 201580068469.1 dated Jul. 29, 2019 and its English translation.
Office action from Chinese Patent Application No. 201580068398.5 dated Sep. 29, 2018 and its English translation.
Office action from Chinese Patent Application No. 201580068398.5 dated Aug. 2, 2019 with search report and its English translation.
Office action from Chinese Patent Application No. 201680028488.6 dated Mar. 21, 2019 and its English translation.
Office action from Chinese Patent Application No. 201680028488.6 dated Oct. 9, 2019 and its English translation.
EPO extended search report from European Patent Application No. 15852255.7 dated Dec. 19, 2018.
EPO extended search report from European Patent Application No. 16783528.9 dated Jan. 7, 2019.
Office action from Chinese Patent Application No. 201580068469.1 dated Apr. 14, 2020.
Office action from Chinese Patent Application No. 201580068398.5 dated Apr. 27, 2020.
Office action from Chinese Patent Application No. 201680028488.6 dated May 29, 2020.
Epo extended Search Report from European Patent Application No. 15852048.6 dated Jun. 8, 2018.
From U.S. Appl. No. 15/751,150, Office Action dated Apr. 13, 2020.
From U.S. Appl. No. 15/751,150, Office Action dated Oct. 2, 2020.
EPO extended search report from European Patent Application No. 20020249.7 dated Oct. 9, 2020.
Office action from Chinese Patent Application No. 201580068469.1 dated Jan. 6, 2021, and its English translation.
Office action from Chinese Patent Application No. 201580068398.5 dated Feb. 1, 2021, and its machine English translation.

* cited by examiner

STEERABLE MICRO-ENDOSCOPE

CROSS REFERENCE TO RELATED APPLICATIONS

This application claims priority to and claims the benefit of U.S. Application Ser. No. 62/066,340 filed Oct. 20, 2014, and PCT Application PCT/US2015/027170, filed on Apr. 22, 2015, which are hereby incorporated by reference in their entireties.

FIELD OF THE DISCLOSURE

The present disclosure relates to steerable micro devices such as medical catheters or endoscopes of reduced size, and methods of making thereof.

BACKGROUND

Various commercially available catheters and endoscopes exist for introducing into the body vessels and cavities a variety of surgical tools, fluids, and other materials, such as radiographic contrast materials, angioplasty balloons, fiberoptic scopes, laser lights, and cutting instruments. Also, various techniques and systems have been developed for guiding or steering the catheters in the body vessels and cavities for use of these tools, fluids, and other materials.

Examples of such guiding or steering techniques and systems for catheters or endoscopes may be seen in: U.S. Pat. No. 5,342,299 to Snoke entitled "steerable catheter"; in WO2004086957 to Banik, entitled "Single use endoscopic imaging system"; in US20140135576 to Hebert, entitled "Coaxial micro-endoscope"; in U.S. Pat. No. 8,517,921 to Tremaglio, entitled "Endoscopic instrument having reduced diameter flexible shaft"; in U.S. Pat. No. 8,262,563 to Bakos, entitled "Endoscopic translumenal articulatable steerable overtube"; in U.S. Pat. No. 8,320,650 to Demos, entitled "In vivo spectral micro-imaging of tissue"; in US 2008/0319418 to Chong, entitled "Catheter Steering Device"; in WO 02/053221 to Gaber, entitled "Deflectable Guiding Apparatus"; in U.S. Pat. No. 4,580,551 to Siegmund, entitled "Flexible Plastic Tube for Endoscope and the Like"; in U.S. Pat. No. 5,325,845 to Adair, entitled "Steerable Sheath for Use with Selected Removable Optical Catheter"; in U.S. Pat. No. 4,798,193 to Giesy, entitled "Protective Sheath Instrument Carrier"; in U.S. Pat. No. 4,788,967 to Ueda; entitled "Endoscope"; in U.S. Pat. No. 7,033,317 to Pruitt, entitled "disposable endoscope and method of making a disposable endoscope; in U.S. Pat. No. 5,197,457 to Adair, entitled "deformable and removable sheath for optical catheter".

However, there exists a need for a steerable micro-device, such as a micro-endoscope or catheter with a steerable distal end, which would be particularly simple and economical to manufacture.

SUMMARY OF THE DISCLOSURE

An object of the present disclosure relates to a steerable micro-endoscope, preferably having at least a lumen for conducting light to its distal end and a camera at its distal end. Another object of the present disclosure relates to a steerable micro-catheter.

An object of the present disclosure relates to a micro-device that is steerable in that it has an elongated member with a distal portion that bends in a remotely controlled way. An object of the present disclosure relates to a micro-device that is steerable in that it has an elongated member that rotates axially in a controllable way.

An object of the present disclosure relates to a micro-device having a housing of such a size as to be readily held in the hand of a user.

An object of the present disclosure relates to a micro-device that has an elongated member with a diameter of 2 millimeter or less.

These and other objects, features, and advantages are provided in a steerable micro-device comprising a cylindrical elongated member having a distal end and a proximal end, the elongated member comprising at least a first lumen, a tensioning wire running in the first lumen, a distal end of the tensioning wire being attached at the distal end of the elongated member and a proximal end of the tensioning wire exiting the first lumen at the proximal end of the elongated member;

the elongated member having a proximal portion extending from the proximal end toward the distal end of the elongated member and a distal portion extending from the distal end to the proximal portion of the elongated member, the proximal portion having a first durometer ("hard" section) and the distal portion having a second durometer ("soft" section), lower than the first durometer; the first lumen being arranged such that the distal portion of the elongated body bends when the proximal end of the tensioning wire is pulled.

According to an embodiment of the present disclosure, the elongated member is held in an outer tube comprising: a torque tube having an axial lumen with an inner diameter equal to, or slightly larger than, the outer diameter of the elongated member; and a mesh-sheath wound around the torque tube.

According to an embodiment of the present disclosure, the distal end of the elongated member is in contact with the proximal end of a ring structure; the ring structure forming a loop path through which the tensioning wire runs, whereby a pull on the tensioning wire exerts pressure on the distal end of the elongated member around said tensioning wire.

According to an alternative embodiment of the present disclosure, the elongated member is held directly in a torque mesh-sheath wound around the elongated member.

According to an embodiment, the mesh sheath is made of wires having a non-circular cross-section.

According to an embodiment of the present disclosure, the first durometer is chosen such that the proximal portion is flexible enough to be inserted in a desired body cavity without damaging the cavity, and the second durometer is chosen such that when the tensioning wire is pulled, the distal portion bends. According to an embodiment of the present disclosure, the second durometer is chosen such that when the tensioning wire is relaxed after having been pulled, the distal portion tends to return to an unbent shape.

According to an embodiment of the present disclosure, the torque mesh-sheath is covered by an outer sheath. The outer sheath can be made out of a shrink-wrap tube, or can be made using a continuous process such as by dipping into a coating bath.

According to an embodiment of the present disclosure, the elongated member comprises a second lumen; an optical fiber arranged in the second lumen having a proximal end capable of receiving light from a source of light and a distal end capable of emitting light received at the proximal end from the distal end. According to an embodiment of the present disclosure, the proximal end of the optical fiber is coupled with a connector for interfacing with a source of light. According to an embodiment of the present disclosure, the elongated member comprises at least two second lumens arranged on both sides of the first lumen along a diameter around the axis of the elongated member.

According to an embodiment of the present disclosure, the elongated member comprises a third lumen and the distal end of the elongated member comprises a camera, at least a first wire of the camera running through the third lumen. According to an embodiment of the disclosure, a second wire of the camera runs through the third lumen. According to an embodiment of the present disclosure, the proximal ends of the wires of the camera are coupled to a connector for interfacing with an imaging device. According to an embodiment of the present disclosure, the camera is aligned along the axis of the elongated member.

According to an embodiment of the present disclosure, the distal end of the distal portion comprises a head made in a material different from the material of the elongated member, a distal portion of the head having the same cross section as the elongated member with the torque mesh sheath and the outer sheath or jacket. A proximal portion of the head can be provided for being inserted in an appropriate cavity formed at the distal end of the elongated member. According to an embodiment of the present disclosure, the distal end of the tensioning wire is attached to the head. According to an embodiment of the present disclosure, the camera is held in the head. According to an embodiment of the present disclosure, the camera comprises at least an electronic sensor and a lens. According to an embodiment of the present disclosure, the head comprises at least one lumen through which passes the distal end of the optical fiber.

According to an embodiment of the present disclosure, the elongated member comprises a fourth lumen enabling to pass a fluid from the proximal end to the distal end of the elongated member.

According to an embodiment of the present disclosure, the elongated member has a circular cross-section with a diameter lower than 2 millimeter. According to an embodiment of the present disclosure, the elongated member has a diameter lower than 1 millimeter. According to an embodiment of the present disclosure, the elongated member has a non circular cross-section with a maximum dimension lower than 2 millimeter. According to an embodiment of the present disclosure, the elongated member has a cross-section with a maximum dimension lower than 1 millimeter.

According to an embodiment of the present disclosure, the tensioning wire has a diameter of 0.15 millimeter or less.

According to an embodiment of the present disclosure, the elongated member comprises two first lumen containing each a tensioning wire, wherein the distal ends of the tensioning wires in the two first lumens are joined together.

According to an embodiment of the present disclosure, the tensioning wire is coated with a lubricant and is in direct contact with the inner walls of the first lumen.

According to an embodiment of the present disclosure, the elongated member and any lumen in the elongated member are formed by extrusion or any appropriate continuous manufacturing process.

According to an embodiment of the present disclosure, the proximal end of the elongated member is attached to a base that is rotatable with respect to a proximal housing around an axis of the proximal end of the elongated member. According to an embodiment of the present disclosure, the base is rotatable manually. According to an embodiment of the present disclosure, the base comprises a lock for controllably locking the base rotated along a desired angle. According to an embodiment of the present disclosure, the base comprises a knob for controllably rotating the base.

According to an embodiment of the present disclosure, the housing comprises a lever for controllably pulling on the proximal end of the tensioning wire. According to an embodiment of the present disclosure, the lever comprises a lock for locking the tensioning wire pulled along a desired length. According to an embodiment of the present disclosure, the tensioning wire passes through a flexible sheath that is not compressible axially between the base and the lever. According to an embodiment of the present disclosure, the tensioning wire is coupled to the lever using cogwheels or gears. According to an embodiment of the present disclosure, the ratio between the cogwheels or gears can be changed to adjust the sensitivity of the lever.

According to an embodiment of the present disclosure, the housing is shaped for being held in one hand, such that the lever can be actuated by tightening the grip of the hand and the base can be rotated by actuation of a knob with the thumb of the hand.

According to an embodiment of the present disclosure, the elongated member comprises two first lumen containing each one tensioning wire, the two first lumens being arranged on diametrically opposed sides of the axis of the elongated member. According to an embodiment of the present disclosure, the lever of the housing is arranged such that pressing one end of the lever pulls on the proximal end of the tensioning wire in one of the first lumens and pressing another end of the lever pulls on the proximal end of the tensioning wire in the other of the first lumens.

According to an embodiment of the present disclosure, the elongated member has a circular cross section.

According to an embodiment of the present disclosure, the elongated member has an elliptic cross section.

According to an embodiment of the present disclosure, the elongated member has a cross section comprising two half circles joined by straight lines.

According to an embodiment of the present disclosure, the proximal portion and the distal portion of the elongated member are extruded out of two different materials and are assembled together after extrusion.

According to an embodiment of the present disclosure, the proximal portion and the distal portion of the elongated member are made out of a single material; a sheath being inserted in at least one lumen of the elongated member along the proximal portion of the elongated number to increase the durometer of the proximal portion with respect to the durometer of the distal portion.

According to an embodiment of the present disclosure, the proximal portion and the distal portion of the elongated member are made out of a single material; and matter is removed from the elongated member in the distal portion to lower the durometer of the distal portion with respect to the durometer of the proximal portion. According to an embodiment of the present disclosure, matter is removed from the elongated member in the distal portion by forming at least one cut in a plane that does not comprise the axis of the elongated member. According to an embodiment of the present disclosure, matter is removed from the elongated member in the distal portion by forming at least one bore along an axis that differs from the axis of the elongated member. According to an embodiment of the present disclosure, matter is removed from the elongated member in the distal portion by treating chemically the distal portion.

DETAILED DESCRIPTION

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention. The same references designate the same elements in the figures.

Figure 1:
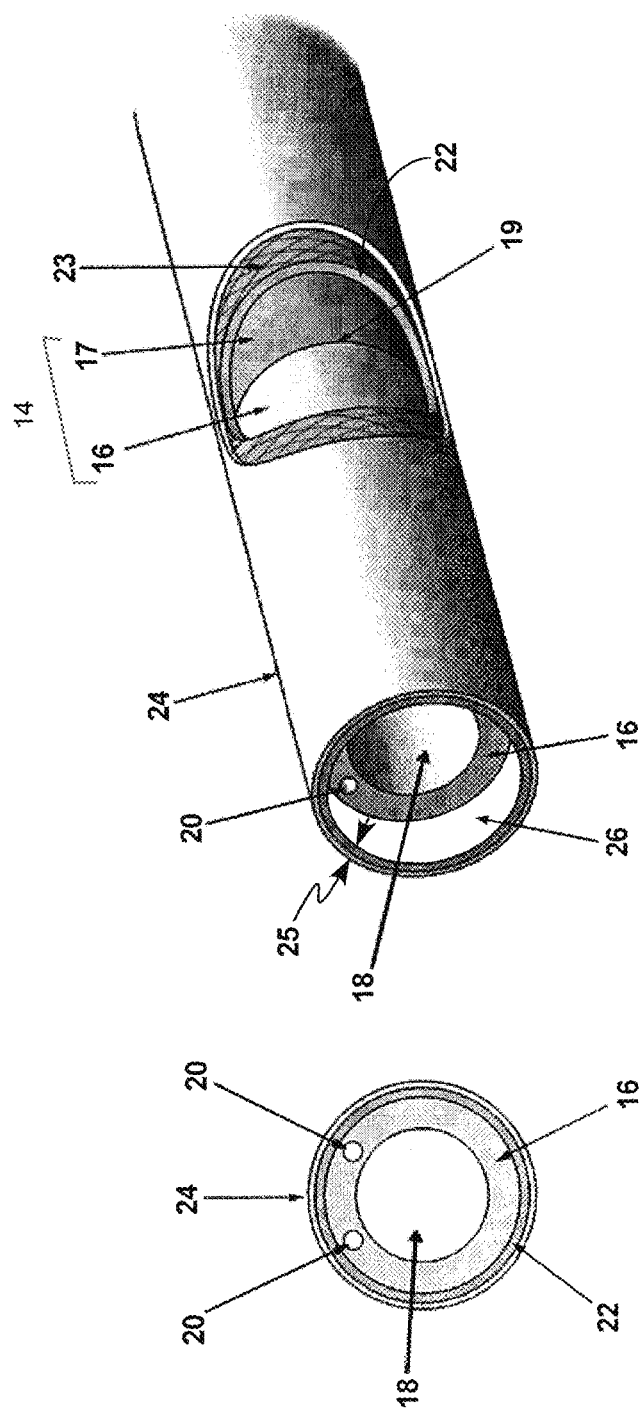
FIG. 1 details the structure of proximal and distal portions of a cylindrical elongated member of a steerable microdevice according to an embodiment of the present disclosure.

FIG. 1 shows a front view and an elevation view of the distal portion 16 and proximal portion 17 of a cylindrical elongated member 14 of a steerable micro-device (not shown) according to an embodiment of the present disclosure.

According to an embodiment of the present disclosure, elongated member 14 comprises a micro-extruded distal portion 16, having a first durometer, and a micro-extruded proximal portion 17 having a second durometer, higher than the first durometer. According to an embodiment of the present disclosure, elongated member 14 comprises a main lumen 18 of the elongated member, through which for example a camera cable can run. The extruded distal portion 16 can be glued or thermal bonded to the extruded proximal portion 17 at a bonding line 19. According to an embodiment of the present disclosure, extruded distal portion 16 can be simply abutted to the extruded proximal portion 17 at line 19. According to an embodiment of the present disclosure, elongated member 14 comprises at least one secondary lumen 20, through which a tensioning wire (not shown) can run. The tensioning wire can be attached at the distal end of the elongated member 14 and a proximal end of the tensioning wire can exit the secondary lumen at the proximal end (not shown) of the elongated member. According to an embodiment of the present disclosure, elongated member 14 is sheathed in a torque tube 22. According to an embodiment of the present disclosure, torque tube 22 is a hollow tube (i.e. a tube with a large axial lumen) that can be manufactured by extrusion. According to an embodiment of the present disclosure, a torque mesh sheath or torque braid sheath 23 is tightly wound around extruded torque tube 22. According to an embodiment of the present disclosure, torque tube 22 is further sheathed in a jacket or outer sheath 24 tightly arranged around torque braid sheath 23. According to an embodiment of the present disclosure, torque tube 22 is formed by extrusion, then torque braid sheath 23 is wound around torque tube 22 and optionally sheath 24 is arranged tightly around torque braid sheath 23, forming an outer tube 25 having an inner diameter equal to, or slightly larger than, the outer diameter of extruded portions 16 and 17. For example, the inner diameter of outer tube 25 (which is the inner diameter of the axial lumen of tube 22) can be 0 to 60 micrometer (preferably 0 to 50 micrometer) larger than the outer diameter of extruded portions 16 and 17.

According to an embodiment of the present disclosure, extruded portion 17 can have an outer diameter of 1.40 mm, and outer tube 25 can have an inner diameter of 1.40 min to 1.460 mm. The inventors have noted with surprise that a tube having a given outer diameter can efficiently be slid inside an outer tube having an inner diameter identical to, or slightly larger (0 to 60 micrometer larger) than said given outer diameter.

According to an embodiment of the present disclosure, extruded portion 17 is pulled inside outer tube 25. According to an embodiment of the present disclosure, extruded portion 17 is made of a resilient material, whereby the pulling of extruded portion 17 slightly elongates extruded portion 17, which reduces slightly the diameter of extruded portion 17 and eases the pulling of extruded portion 17 inside outer tube 25.

According to an embodiment of the present disclosure, the distal end of the sheathed elongated member 14 can comprise a recess 26 formed by the extruded distal portion 16 of elongated member 14 being shorter than outer tube 25. The recess 26 can be used for receiving a narrow proximal portion of a distal head (not shown) of the steerable micro-device. According to an embodiment of the present disclosure, recess 26 can be obtained by introducing the proximal end of extruded portion 17 into the distal end of outer tube 25, and pulling the proximal end of extruded portion 17 into outer tube 25 until the distal end of extruded portion 17 passes the distal end of outer tube 25.

In an embodiment where extruded portion 16 is attached to the distal end of extruded portion 17, extruded portion 17 is pulled inside outer tube 25 until the distal end of extruded portion passes the distal end of outer tube 25 and forms recess 26. In an embodiment where extruded portion 16 is not attached to the distal end of extruded portion 17, extruded portion 17 is pulled inside outer tube 25 until there is room inside the distal end of outer tube 25 for extruded portion 16 and recess 26.

According to an embodiment of the present disclosure, the proximal portion and the distal portion of the elongated member are extruded out of two different materials and are assembled together after extrusion. According to an embodiment of the present disclosure, the extruded distal portion 16 of the elongated member can be made of Polyether Block Amide (PEBA) or polyurethane for the portion having the lower durometer, with for example a durometer of 40 to 25 and the extruded proximal portion 17 of the elongated member can be made of Polyether Block Amide (PEBA) or polyurethane with for example a durometer of 80 to 75.

According to an embodiment of the present disclosure, torque mesh-sheath 23 is made of wires having a non-circular cross-section. According to an embodiment of the present disclosure, the secondary lumen 20 is arranged such that the distal portion 16 of the elongated body bends when the proximal end of the tensioning wire (not shown) is pulled.

According to an embodiment of the present disclosure, the first durometer is chosen such that the proximal portion 17 is flexible enough to be inserted in a desired body cavity without damaging the cavity, and the second durometer is chosen such that the distal portion 16 bends when the tensioning wire is pulled.

According to an embodiment of the present disclosure, the second durometer is chosen such that when the tensioning wire (not shown) is relaxed after having been pulled, the distal portion 16 tends to return to an unbent shape.

According to an embodiment of the present disclosure, the elongated member comprises at least two secondary lumens 20 and an optical fiber (not shown) is arranged in the second secondary lumen 20, the optical fiber having a proximal end capable of receiving light from a source of light and a distal end capable of emitting light received at the proximal end from the distal end. The proximal end of the optical fiber can be coupled with a connector for interfacing with a source of light.

Figure 2:
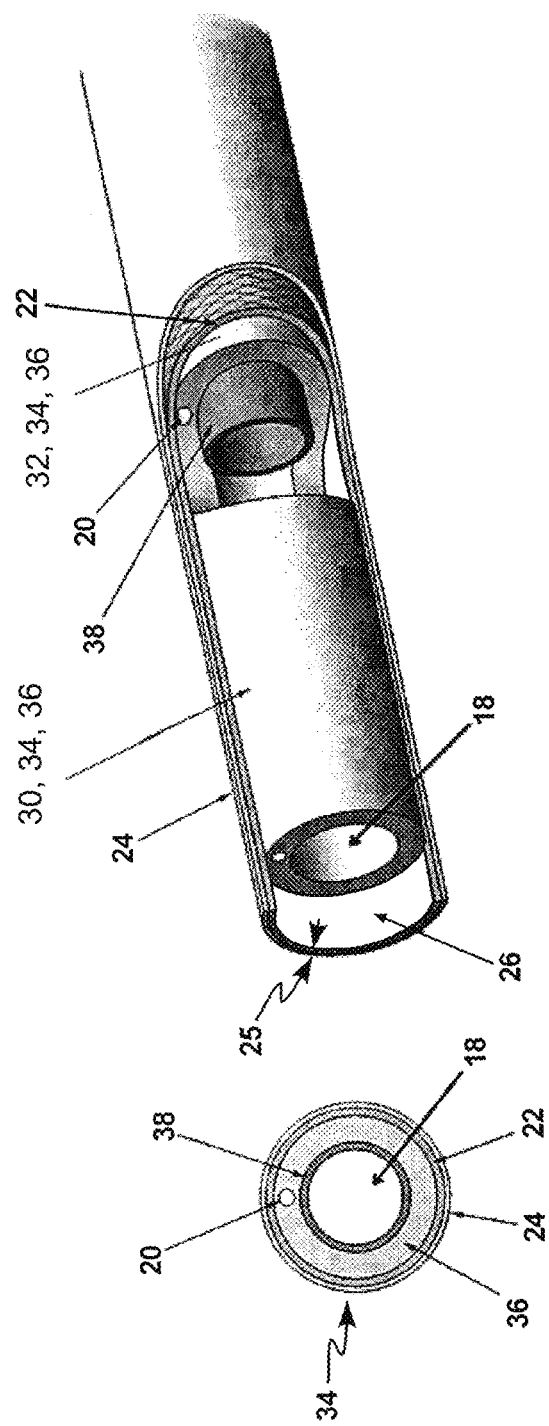
FIG. 2 details the structure of proximal and distal portions of a cylindrical elongated member of a steerable micro-device according to an embodiment of the present disclosure.

FIG. 2 shows a front view and an elevation view of the distal portion 30 and proximal portion 32 of a cylindrical elongated member 34 of a steerable micro-device (not shown) according to an embodiment of the present disclosure.

According to an embodiment of the present disclosure, the proximal portion 32 and the distal portion 30 of the elongated member 34 are made out of a single material tube 36 (for example using micro-extrusion), and an inner sheath or tube 38 is inserted in at least one lumen of the elongated member 34, for example first lumen 18, along the proximal portion 32 of the elongated member 34 to increase the durometer of the proximal portion 32 with respect to the durometer of the distal portion 30. Elongated member 34 is introduced into outer tube 25 after separate manufacturing of both the elongated member 34 and the outer tube 25.

Figure 3:
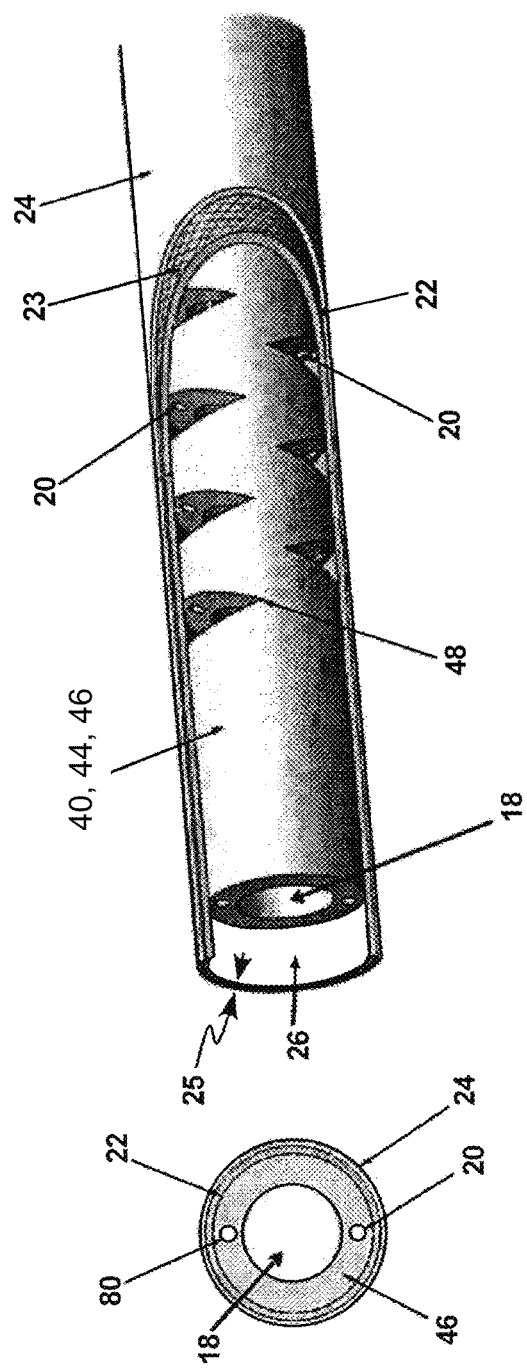
FIG. 3 details the structure of proximal and distal portions of a cylindrical elongated member of a steerable micro-device according to an embodiment of the present disclosure.

FIG. 3 shows a front view and an elevation view of a distal portion 40 of a cylindrical elongated member 44 of a steerable micro-device (not shown) according to an embodiment of the present disclosure. The same references designate the same elements in FIG. 1 and FIG. 3.

According to an embodiment of the present disclosure, a proximal portion 42 (not shown) and the distal portion 40 of the elongated member 44 are made out of a single material tube 46 (for example using micro-extrusion), and matter is removed from tube 46 in the distal portion, forming recesses or notches 48, to lower the durometer of the distal portion 40 with respect to the durometer of the proximal portion.

FIGS. 4A-D illustrate steps of manufacturing of the cylindrical elongated member of FIG. 3.

Figure 4A:
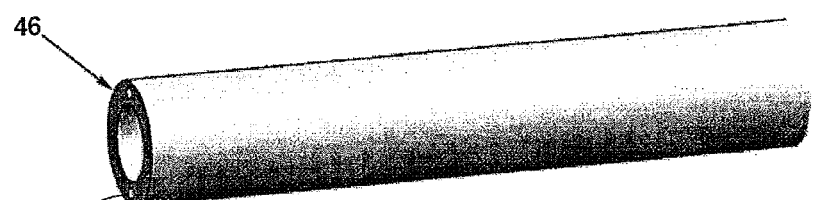
FIGS. 4A-D illustrate steps of manufacturing of the cylindrical elongated member of FIG. 3.

FIG. 4A shows an elevation view of a micro-extruded tube 46 before cuts or notches 48 are made.

Figure 4B:
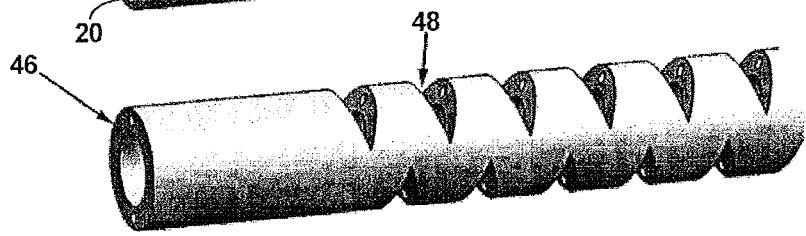

FIG. 4B shows an elevation view of micro-extruded tube 46 after cuts or notches 48 are made. The position of the cuts can vary.

Figure 4C:
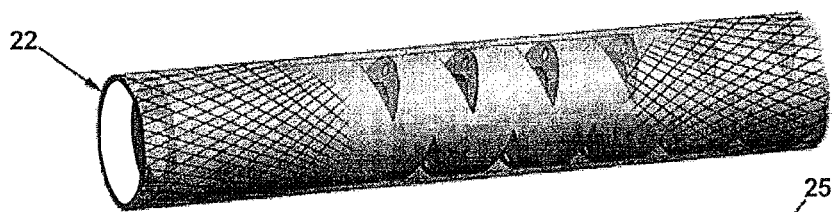

FIG. 4C shows an elevation view of micro-extruded tube 46 inside the torque tube 22.

Figure 4D:
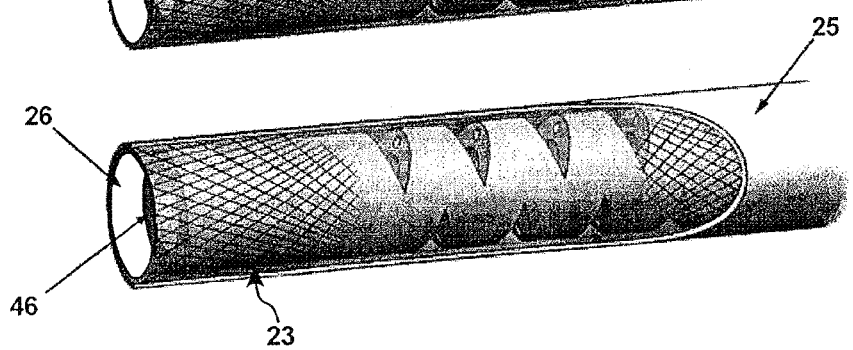

FIG. 4D shows an elevation view of jacket 24 attached around the torque tube 22.

The cuts or notches 48 can be made up to the very tip (not shown) of the tube 46 or stop before (as illustrated) the distal end of the tube 46, so as to keep a stiffer distal tip at the distal end of the tube 46. There are no cuts in the proximal portion (not shown) of the tube 46.

Figure 4E:
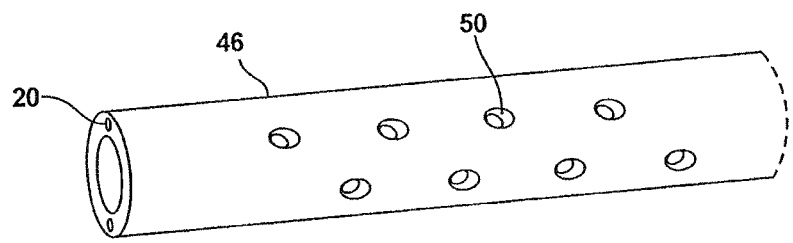
FIGS. 4E-F illustrate alternate steps of manufacturing of the cylindrical elongated member of FIG. 3.

FIG. 4E shows an elevation view of micro-extruded tube 46 wherein, according to an alternative embodiment of the present disclosure, the cuts or notches 48 are replaced by bores 50 along an axis that differs from the axis of the elongated member.

Figure 4F:
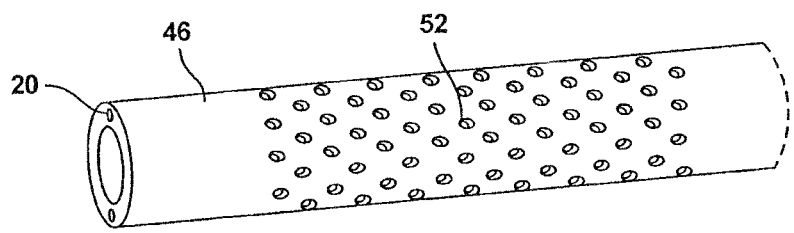

FIG. 4F shows an elevation view of micro-extruded tube 46 wherein, according to an alternative embodiment of the present disclosure, the cuts or notches 48 are replaced by micro-holes 52 obtained by treating chemically a desired portion of micro-extruded tube 46.

Figure 5:
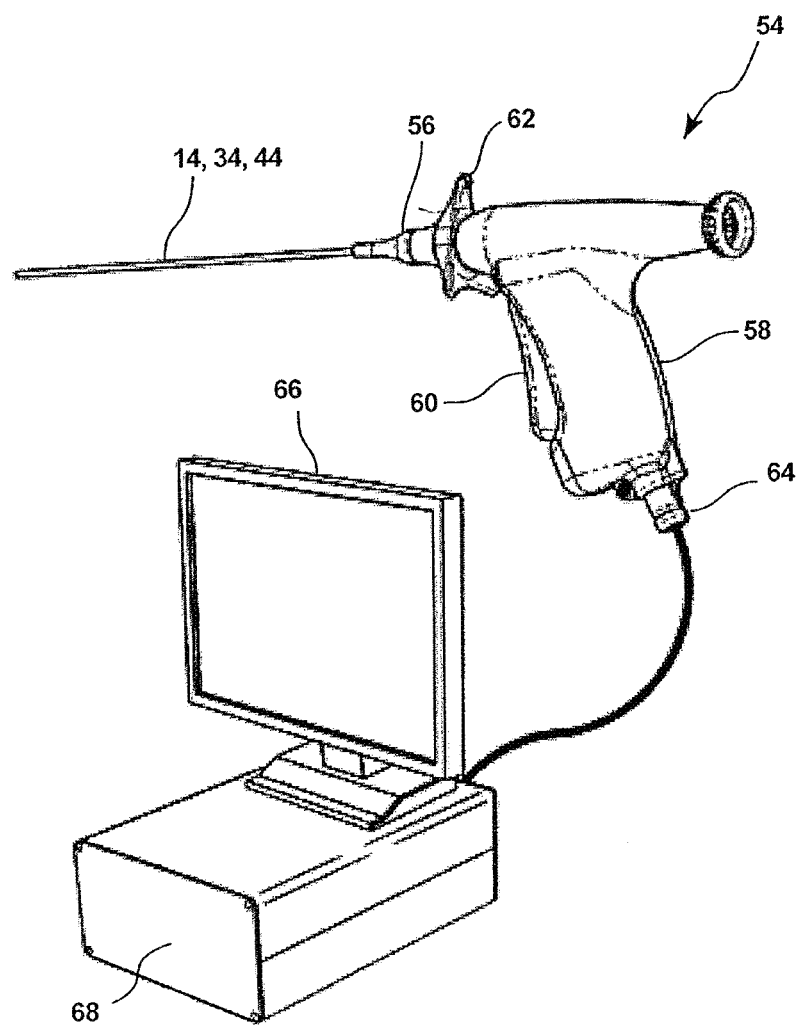
FIG. 5 is an elevation view of a steerable micro-device according to an embodiment of the present disclosure.

FIG. 5 is an elevation view of a steerable micro-device 54 according to an embodiment of the present disclosure, wherein the proximal end of the elongated member (such as the elongated member 14, 34 or 44 of FIGS. 1-3) is attached to a base 56, itself attached to a proximal housing. According to an embodiment of the present disclosure, the housing can comprises a connector 64 for coupling a camera located at the distal end of the elongated member (14, 34, 44) with an imaging device 66 and a source of power and/or light 68.

Figure 6:
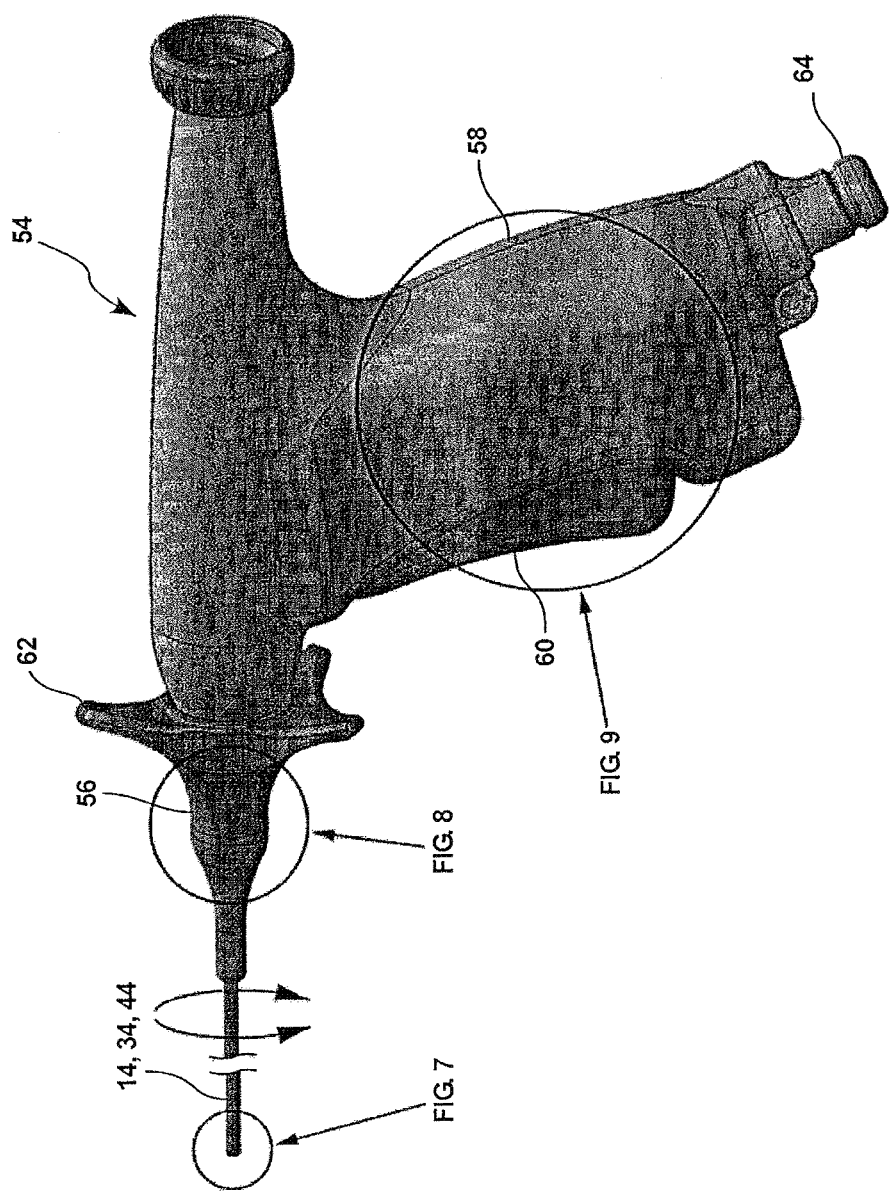
FIG. 6 is a close-up elevation view of the steerable micro-device of FIG. 5.

FIG. 6 is a close-up elevation view of the steerable micro-device of FIG. 5.

Preferably, base 56 is rotatable with respect to the housing around an axis of the proximal end of the elongated member (14, 34 or 44). According to an embodiment of the present disclosure, the housing comprises a lever for controllably pulling on the proximal end of the tensioning wire in lumen 20. According to an embodiment of the present disclosure, the housing can be shaped as a handle or can comprise a handle 58. According to an embodiment of the present disclosure, handle 58 comprises a trigger-shaped lever 60 that allows pulling on the tensioning wire in lumen 20 by tightening the grip on the handle. Lever 60 can comprise a lock for locking the tensioning wire pulled along a desired length.

According to an embodiment of the present disclosure, base 56 is rotatable manually. According to an embodiment of the present disclosure, a knob such as a three-branched knob 62 is coupled to the base 56 of the elongated member (14, 34, 44) to allow rotating axially the elongated member.

According to an embodiment of the present disclosure, base 56 comprises a lock for controllably locking base 56 rotated along a desired angle. According to an embodiment of the present disclosure, the lock can be actuated by moving base 56 axially toward or away from the housing. According to an embodiment of the present disclosure, the lock can also be located on the housing.

According to an embodiment of the present disclosure, housing 58 is shaped for being held in one hand, such that lever 60 can be actuated by tightening the grip of the hand and base 56 can be rotated by actuation of knob 62 with the thumb of the hand.

Figure 7:
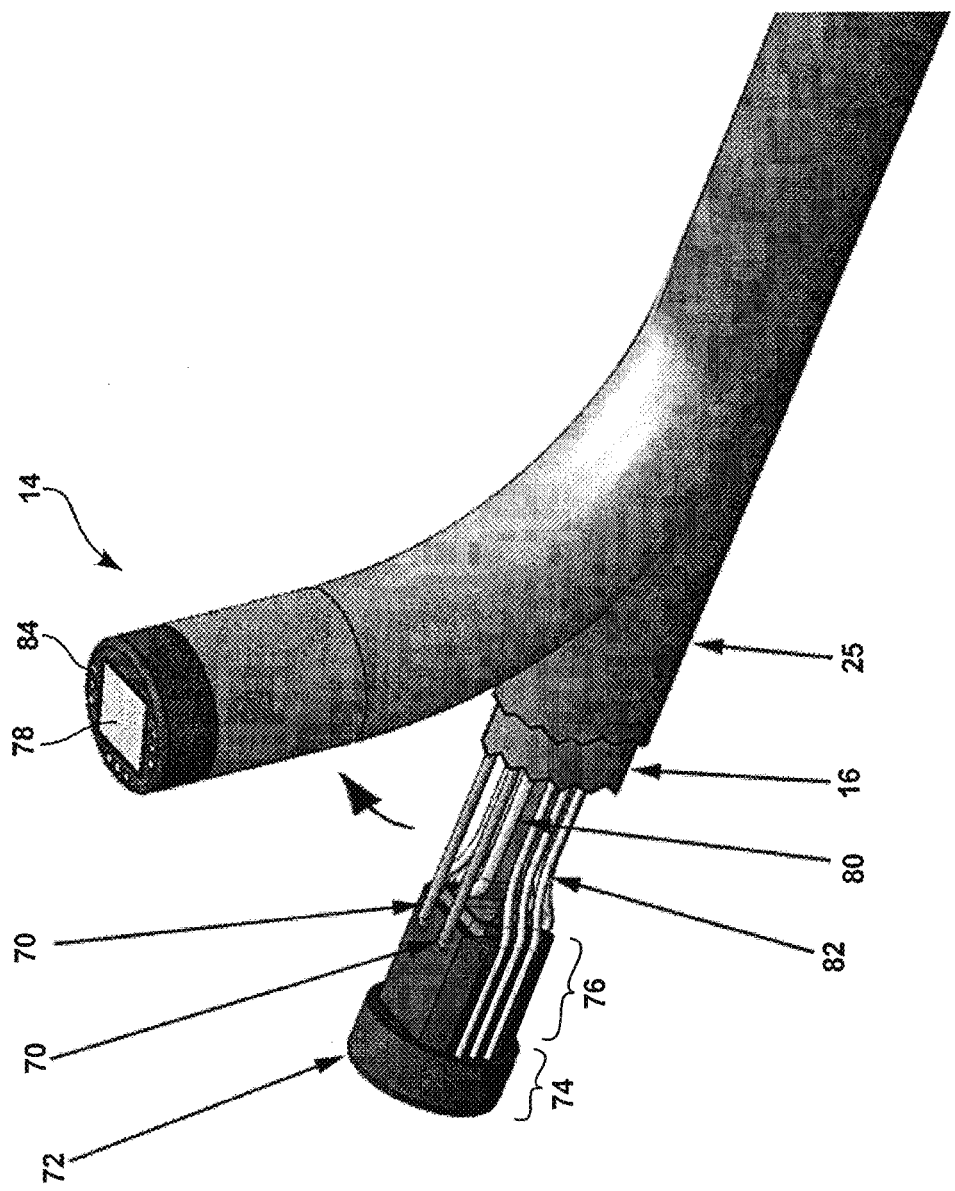
FIG. 7 details the structure of the distal end of a steerable micro-device according to an embodiment of the present disclosure in an unbent position and shows an elevation view of the same distal end in a bent position.

FIG. 7 shows the distal portion 1610 of the sheathed elongated member 14 in an unbent position, with distal parts of extruded distal portion 16 and outer tube 25 removed for clarity of illustration. FIG. 7 also shows the distal portion 16 of sheathed elongated member 14 in a bent position, in result to the pulling of a proximal end (not shown) of at least one tensioning wire 70 that runs in secondary lumen 20. In the example illustrated in FIG. 7, elongated member 14 comprises two secondary lumens 20 side by side (not shown) in which two tensioning wires 70 run side by side. According to an embodiment of the present disclosure, the first lumens 20 are arranged such that the distal portion 16 of elongated body 14 bends when the proximal ends of the tensioning wires are pulled; while the proximal portion 17 of elongated body 14 remains unbent due to the difference in durometer of the distal and proximal portions. According to an embodiment of the present disclosure, the material of extruded distal portion 16 is provided such that, when tensioning wires 70 are released, distal portion 16 returns toward an unbent position such as shown in FIG. 7. According to an embodiment of the present disclosure, each tensioning wire 70 is coated with a lubricant and is in direct contact with the inner walls of its lumen 20. According to an embodiment of the present disclosure, pulling tensioning wires 70 bends the distal portion 16 of elongated member 14 generally toward the tensioning wires 70 along a plane passing through the axis of elongated member 14 in unbent position and passing between tensioning wires 70.

According to an embodiment of the present disclosure, a distal end of the distal portion 16 of sheathed elongated member 14 is attached to a head 72 made of a material different from the material of distal portion 16 of the elongated member. Preferably, a distal portion 74 of the head 72 has the same cross section as the sheathed elongated member 14, such that distal portion 74 seamlessly extends the portion of sheathed elongated member 14. Preferably, a proximal portion 76 of the head 72 is provided for fitting in the cavity 26 shown in FIG. 1. Head 72 can be attached to the sheathed elongated member 14 for example by gluing the proximal portion 76 of the head 72 in cavity 26. According to an embodiment of the present disclosure, the distal end of tensioning wires 70 are attached to head 72. According to an embodiment of the present disclosure, the distal ends of the tensioning wires 70 are joined together (i.e. form a single wire) and run through a loop hole inside the proximal portion 76 of the head 72.

According to an embodiment of the present disclosure, the head 72 comprises a camera 78. Preferably, camera 78 has a distal surface, or window, flush with the distal end of head 72. According to an embodiment of the present disclosure, camera 78 has a longitudinal axis that is aligned with the axis of distal portion 16 of elongated member 14. According to an embodiment of the present disclosure, one or more ribbon cables 80 of camera 78 can run through lumen 18. Preferably, any cable 80 is shielded to protect signals sent by the camera from electromagnetic interferences. According to an embodiment of the present disclosure, elongated member 14 can comprise an additional lumen (e.g. one of the two lumens 20 shown in FIG. 1, in a case where elongated member would comprise a single tensioning wire) within which runs a conductor exclusively used by camera 78. According to an embodiment of the present disclosure, the proximal ends of the wires or cables of camera 78 are coupled to a connector, such as connector 64, for interfacing with an imaging device such as imaging device 66.

According to an embodiment of the present disclosure, elongated member 14 can comprise one or more additional lumens (e.g. one of the two lumens 20 shown in FIG. 1, in a case where elongated member would comprise a single tensioning wire) within which run one or more optical fibers 82. In such an embodiment, at least the distal portion 74 of head 72 comprises at least one lumen 84 through which passes the distal end of the optical fiber 82. FIG. 7 shows an embodiment comprising nine optical fibers 82 ending up in nine lumens 84 in the distal portion 74 of head 72. In the illustrated example, three lumens 84 end up on a side of the distal surface of head 72 opposite, with respect to the axis of the camera, the side of head 72 to which the tensioning wires 70 are attached. In the illustrated example, the two times three remaining lumens 84 end up on opposite sides of the bending plane of elongated member 14. According to an embodiment of the present disclosure, the proximal ends of the optical fibers 82 are coupled to a connector, such as connector 64, for interfacing with a source of power and/or light such as source 68.

According to an embodiment of the present disclosure, sheathed elongated member 14 has a circular cross-section with a diameter lower than 2 millimeter; preferably a diameter lower than 1 millimeter. According to an embodiment of the present disclosure, tensioning wire 70 has a diameter of 0.15 millimeter or less.

According to an embodiment of the present disclosure, camera 78 can be replaced by a lens arrangement, in which case cable 80 can be replaced by a fiber optics bundle for transmitting to the proximal end of the elongated member light entering the lens at the distal end of the elongated member.

Figure 8:
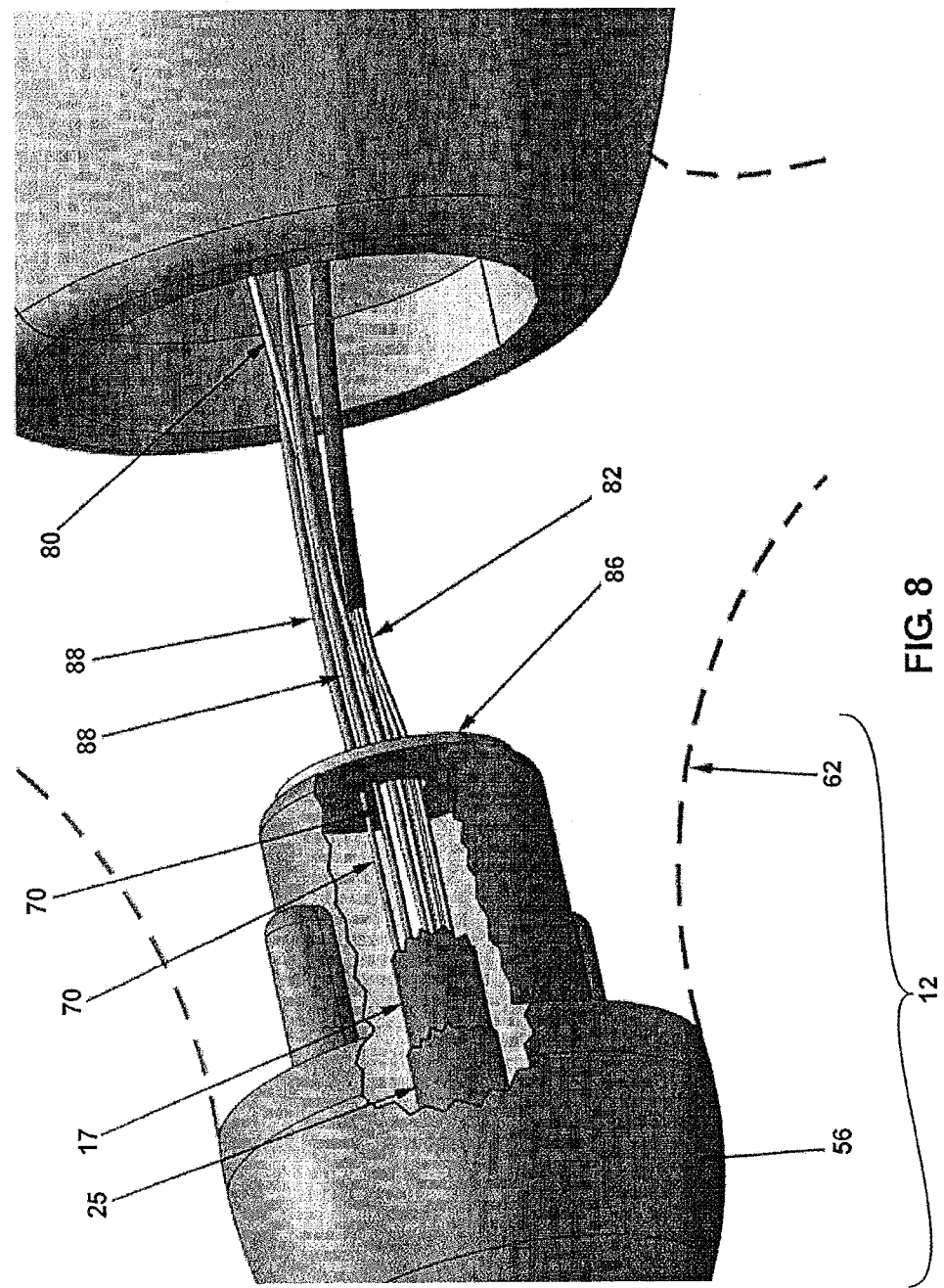
FIG. 8 details the structure of the basis of the elongated member shown in FIGS. 5-6.

FIG. 8 details an exemplary structure of basis 56, to which is attached the proximal end of elongated member 14 as shown in FIGS. 5-6. According to an embodiment of the present disclosure, elongated member is 14 held or sheathed in an outer tube 25 such that an axial rotation of the proximal end of the proximal portion of the sheathed elongated member 14 results in an axial rotation of the distal end of the proximal portion of the sheathed elongated member 14. The outer tube 25 is also provided for compressing along a direction axial to the sheath, thus allowing the distal portion 16 of the elongated member 14 to bend. According to an embodiment of the present disclosure, the wire used to manufacture the torque braid sheath or torque mesh sheath of outer tube 25 has a non circular cross section as this improves the torque transmission provided by the torque braid sheath or torque mesh sheath. FIG. 8 shows the proximal end of the proximal portion 17 of sheathed elongated body 14, with the proximal parts of the extruded proximal portion 17, and of outer tube 25 removed for clarity. According to an embodiment of the present disclosure, the proximal end of proximal portion 17 abuts a stop washer 86 attached to a proximal end of base 56. According to an embodiment of the present disclosure, tensioning wires 70 (two shown in FIG. 8) pass each though dedicated holes through washer 86, whereas camera cable 80 and optical fibers 82 pass through washer 86 though a common wide hole. According to an embodiment of the present disclosure, the proximal ends of the tensioning wires 70 pass through push-tubing 88, the distal extremities of which abut washer 86. FIG. 8 further shows in phantom lines some outlines of knob 62, which rotatably couples base 56 to the housing of the device. According to an embodiment of the present disclosure, base 56 is arranged to rotate axially approximately 178 degrees in either direction with respect to the housing.

Figure 9:
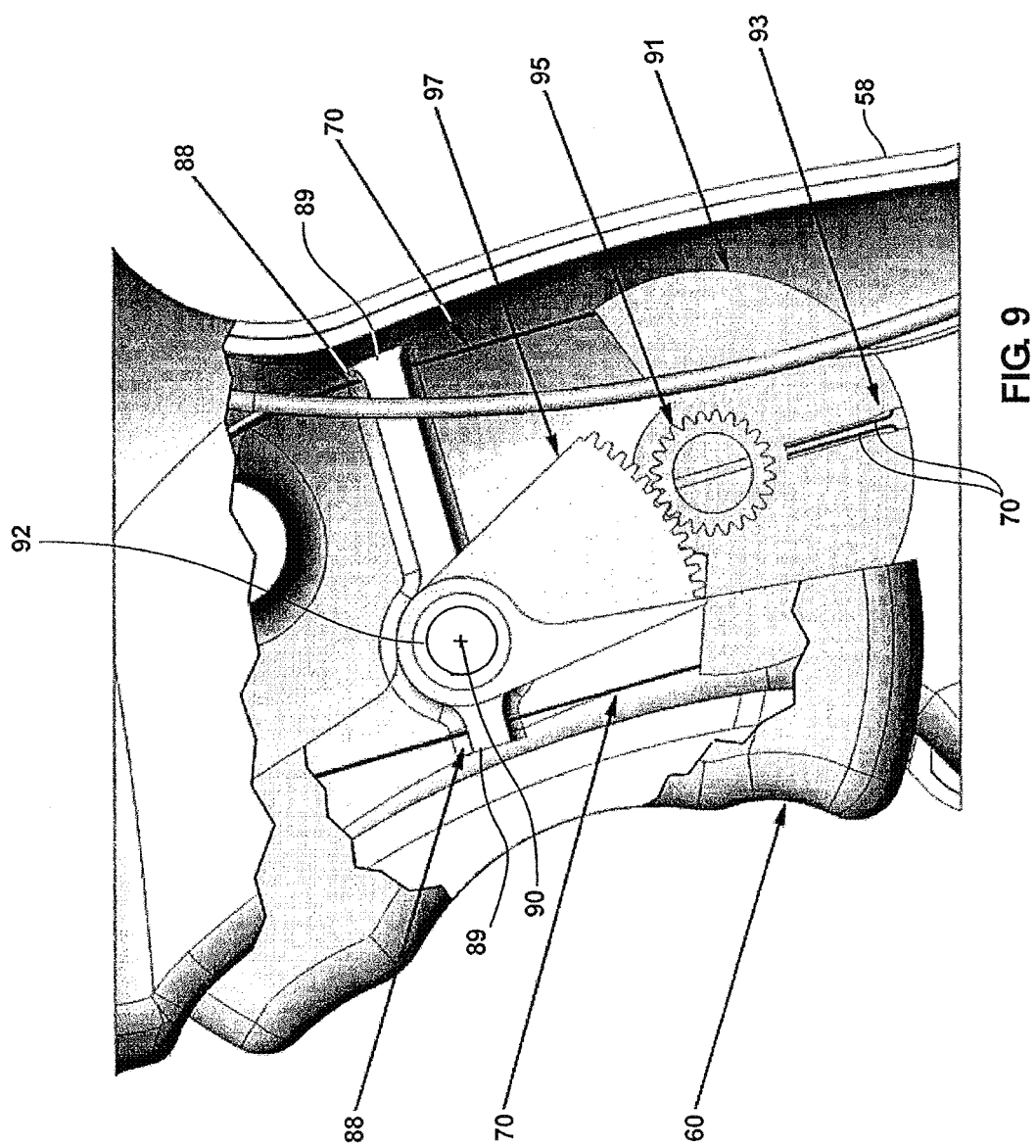
FIG. 9 details the structure of a housing of a steerable micro-device according to an embodiment of the present disclosure.

FIG. 9 details an exemplary structure of a housing of steerable micro-device 54 of FIG. 6, and in particular of handle 58 of the housing. The inside of handle 58 comprises stop ribs 89 having each a lumen through which the proximal ends of the tensioning wires 70 pass through, wherein the proximal ends of push tubings 88 abut stop ribs 89. The proximal ends of the tensioning wires 70 are anchored to a rocker element 91, for example using an anchoring slot 93. Rocker 91 comprises a rotor cogwheel or gear 95, which cooperates with a lever gear 97. Lever gear 97 is coupled to lever 60 such that when lever 60 is actuated by the hand of a user, lever 60 pivots around an axis 90 and causes lever gear 97 to also pivot around axis 90. The pivotal of lever gear 97 around axis 90 causes rotor gear 95 and rocker 91 to rotate, thus pulling the proximal end of at least one wire 70 and causing wire 70 to slide within its associated push tubing 88. In the embodiment illustrated in FIG. 9, for ease of handling lever 60 can be actuated clockwise to pull on a first wire 70 and lever 60 can be actuated counter-clockwise to pull on the other wire 70. Because as illustrated in FIG. 7 both wires 70 are located on a same side of the elongated member 14, pulling either of the wires 70 results in bending the distal portion of elongated member 14. At this juncture, it can be noted that arranging a wire 70 on each side of the axis of elongated member 14 would allow controllably bending elongated member toward each of the wires 70 in a plane comprising the two wires 70. According to an embodiment of the present disclosure, the steering ration of rotor gear 95 can be controllably changed to change the steering sensitivity of the distal portion of elongated member 14. Lever 60 can comprise a lock that allows locking lever 60 in a given position. According to an embodiment of the present disclosure, the lock can be actuated by a pin 92 concentric with axis 90 and passing through the handle 58.

According to an embodiment of the disclosure, the pull wires can be attached directly to lever 60, and thus be actuated directly by lever 60. Alternatively, wires 70 can be actuated by motors; pneumatically; magnetically, etc.

FIGS. 7-9 relate to an embodiment of the present disclosure comprising two wires 70, but embodiments can comprise a single wire 70, for example positioned as any of the two wires 70 of FIGS. 7-9.

Figure 10:
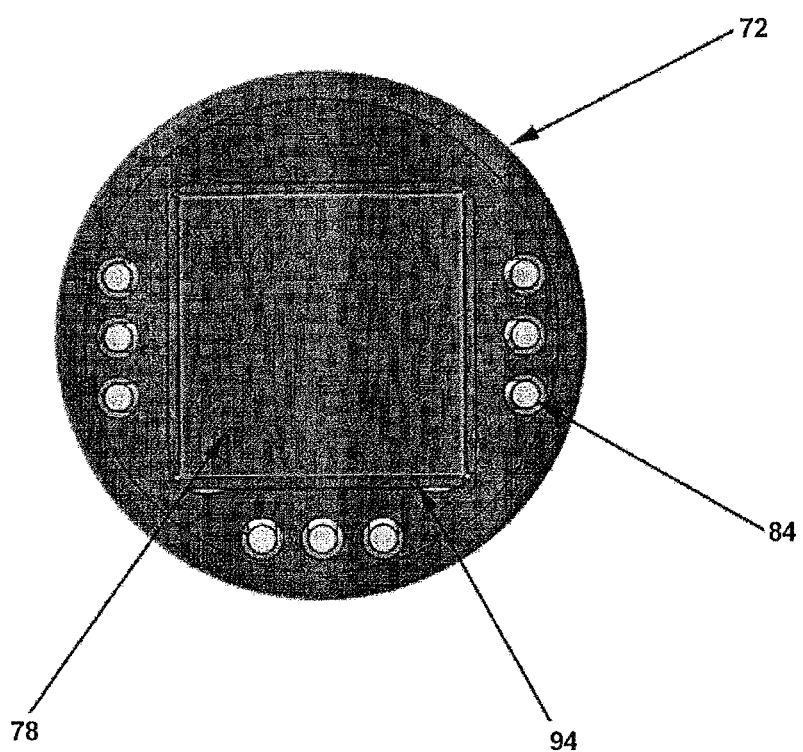
FIG. 10 is a front view of the distal end of a steerable micro-device according to an embodiment of the present disclosure.

FIG. 10 is a front view of the distal end of the head 72 of FIG. 7, showing the distal surface, or window, of camera 78, as well as nine lumens 84. According to an embodiment of the present disclosure, the end of each lumen 84 can comprise a microlens for processing the light output by the optical fiber in the lumen 84. According to an embodiment of the present disclosure, camera 78 can be held in a Faraday shielding box 94, an example of which will be described hereafter. Faraday shielding box 94 can be provided to protect the camera from interferences that may be caused by nearby tools such as electrosurgery tools.

Figure 11A:
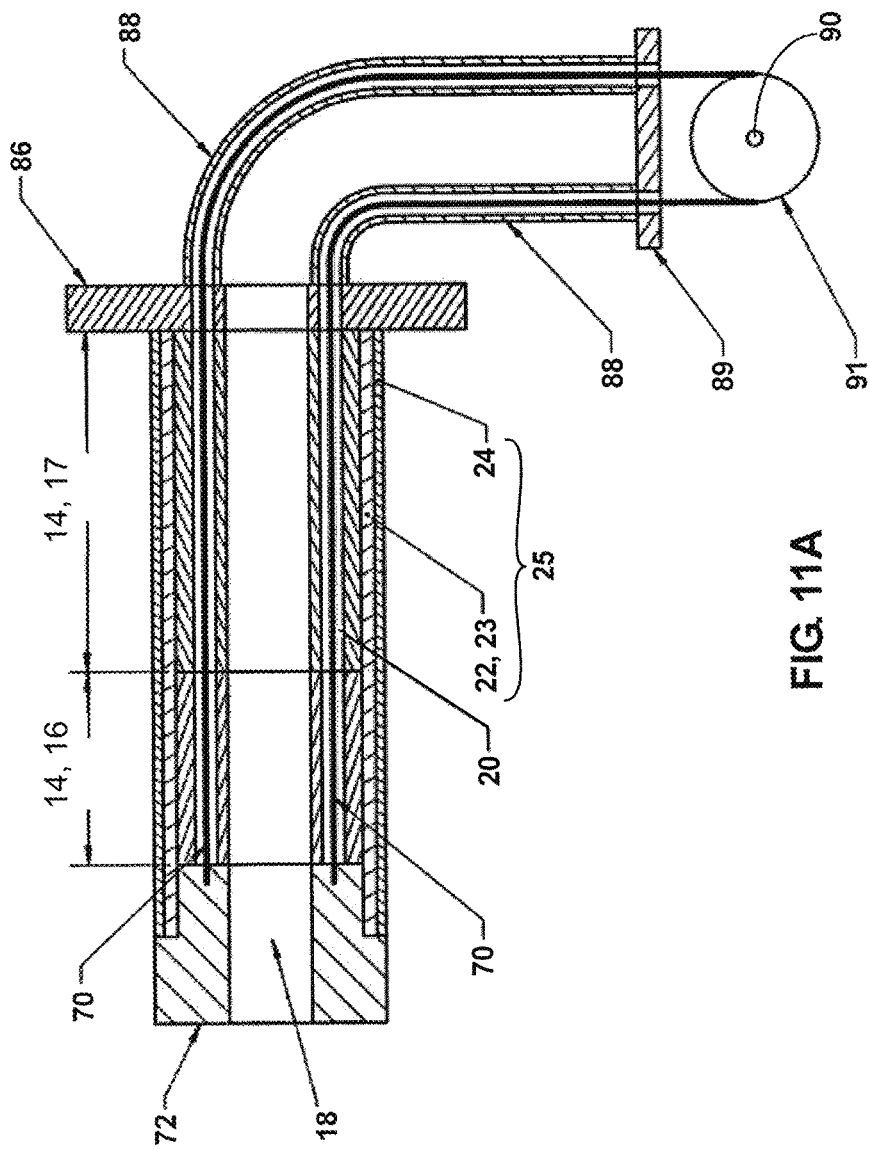
FIG. 11A schematically details the structure of the cylindrical elongated member of a steerable micro-device according to an embodiment of the present disclosure, in an unbent position.

FIG. 11A schematically details the structure of a sheathed elongated member 14 such as shown in FIGS. 6-9, along with some of its actuating features. FIG. 11A shows elongated member 14, having a distal portion 16 and a proximal portion 17, and sheathed in outer tube 25, which comprises a torque tube 22 in a torque mesh sheath 23 and an outer sheath 24. Elongated member comprises a lumen 18 along its axis, and two lumens 20 parallel to lumen 18 and arranged symmetrically with respect to lumen 18. A head 72 capable of holding a micro camera is attached to the distal end of elongated member 14, for example in a recess formed by the torque tube 22, torque mesh tube 23 and outer sheath 24 extending beyond the distal end of elongated member 14. A tensioning wire 70 having a distal end attached to head 72 runs in each lumen 20. A washer 86 is attached to the proximal end of elongated member 14. The proximal portions of the tensioning wires 70 pass through washer 86 and run through push-tubings 88, the distal extremities of which abut washer 86 and the proximal extremities of which abut stop ribs 89. The proximal ends of the tensioning wires 70 pass through holes in stop ribs 89 and are attached to rocker element 91, which can for example be controllably rotated along its axis 90 by a hand-actuated lever (not shown). Washer 86, along with the proximal end of elongated member 14, can for example be controllably rotated around the axis of the proximal end of elongated member 14 using a hand-actuated knob (not shown). According to an embodiment of the present disclosure, torque mesh sheath 23 is made of wires having a non-circular cross-section, to improve transmitting to the distal end of elongated member 14 the rotation torque applied to the proximal end of elongated member 14.

According to an embodiment of the present disclosure, the proximal end of elongated member 14, can be controllably rotated by a motor, a pneumatic actuator, a magnetic actuator, etc.

In FIG. 11A, the tensioning wires 70 are arranged in a plane containing the axis of elongated member 14 (plane of the drawing), thus allowing to bend the distal portion 16 of elongated member 14 in said plane, toward one tensioning wire or the other.

Figure 11B:
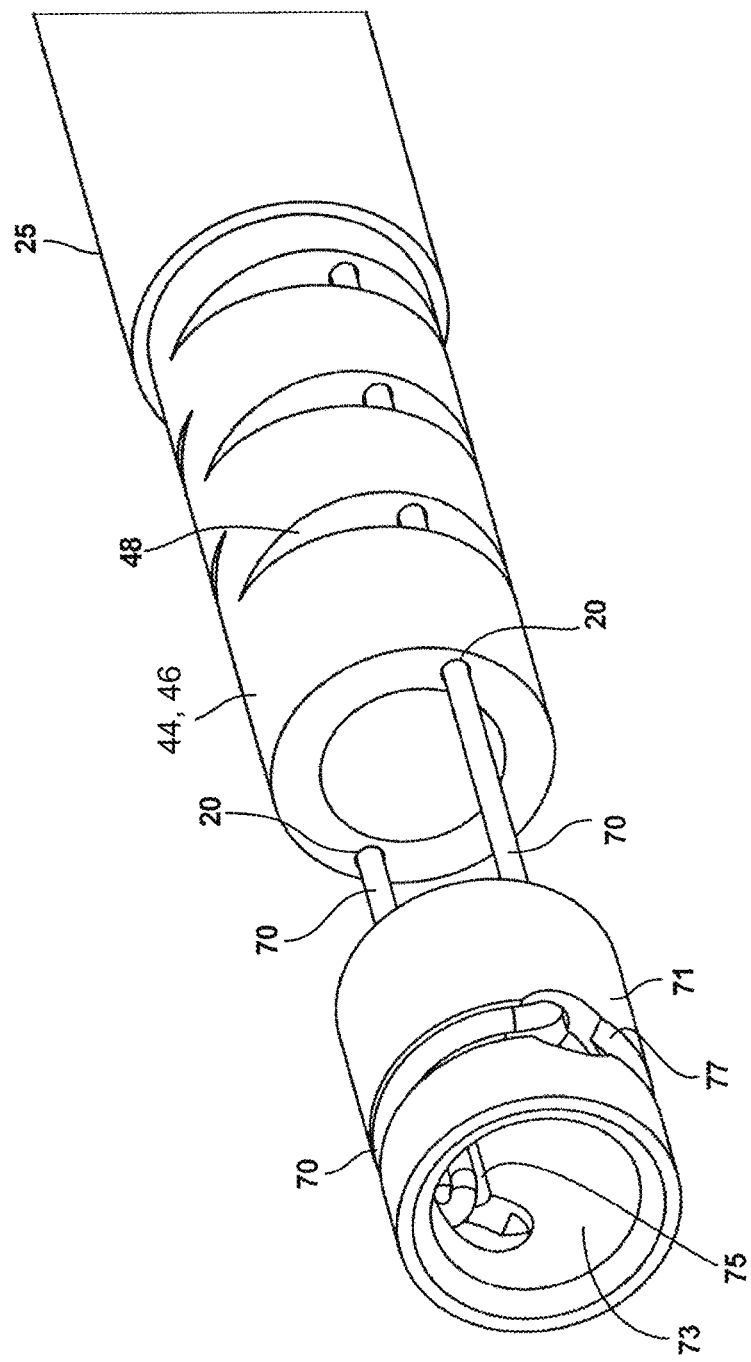
FIG. 11B schematically details the attachment of the pull-wires according to an embodiment of the present disclosure.

FIG. 11B schematically details the attachment of the pull-wires 70 according to an embodiment of the present disclosure. In. FIG. 11B, elongated member 14 of FIG. 11 is replaced by an elongated member 44 such as described in relation with FIGS. 3 and 4A-D. According to an embodiment of the present disclosure where elongated member has at least two lumens 20 for receiving two pull-wires 70, a retaining ring 71 having a cross-section with the same outer dimensions as elongated member 44 is provided at the distal end of elongated member 44. According to an embodiment of the present disclosure, ring 71 comprises an axial lumen 73 having a diameter at least as large as the diameter of the axial lumen of elongated member 44, and two recesses 75 having walls aligned with at least part of the walls of lumens 20 in elongated member 44. Ring 71 also comprises a radial ring recess 77 that runs along an outer diameter of ring 71 at least along one side of ring 71 between the two recesses 75, such that the distal ends of the two wires 70, coming out of lumens 20 of elongated member 44, can run along recesses 75 on the inside of ring 71 until they meet radial ring recess 77 and runs along radial recess 77 on the outside of ring 71, where the distal ends of the two wires 70 meet. According to an embodiment of the present disclosure, the two wires 70 can be a unique wire, a middle portion of which runs along radial ring recess 77 and the extremities of which were passed along recesses 75 and lumens 20 until they exited the lumens 20 at the proximal end of elongated member 44.

According to an embodiment of the present disclosure, ring 71 can be attached (glued; fused; etc.) to the distal end of elongated member 44, or it can be abutted to the distal end of elongated member 44.

In other words, the distal end of the elongated member is in contact with the proximal end of ring structure 71; the ring structure forming a loop path (e.g. recesses 75 and 77) through which the tensioning wire 70 runs, the loop path being provided for preventing the tensioning wire from slipping, whereby a pull on the tensioning wire exerts pressure on the distal end of the elongated member around said tensioning wire.

According to an embodiment of the present disclosure, outer tube 25 can be longer than elongated member 44 and ring 21 together, so as to form a recess 26 as shown for example in FIGS. 1-3. According to an embodiment of the present disclosure, outer tube 25 can have the same length as elongated member 44 and ring 21 together. In such an embodiment, sheathed elongated member 44 (i.e. the elongated member in the outer tube 25) does not comprise a recess 26 as shown for example in FIGS. 1-3, and the axial lumen 73 of ring 71 plays the role of recess 26 as disclosed hereabove, for example for receiving a portion of head 72. According to an embodiment of the present disclosure, when ring 71 is provided at the end of the elongated member, the wires 70 are not attached to the head 72. Head 72 can be attached to the ring 71 (glued, fused, etc.) or can be maintained in ring 71 by attachment to the outer tube 25.

According to an embodiment of the present disclosure, the inner recesses 75 of ring 71 can be lumens if the walls of ring 71 are thick enough. FIG. 11B is illustrated with an elongated member 44 as shown in FIG. 3, but an elongated member 14 or 34 as shown in FIGS. 1 and 2 can indifferently be used in replacement of elongated member 44. Ring 71 can be made of a metal or of a hard plastic.

Figure 12:
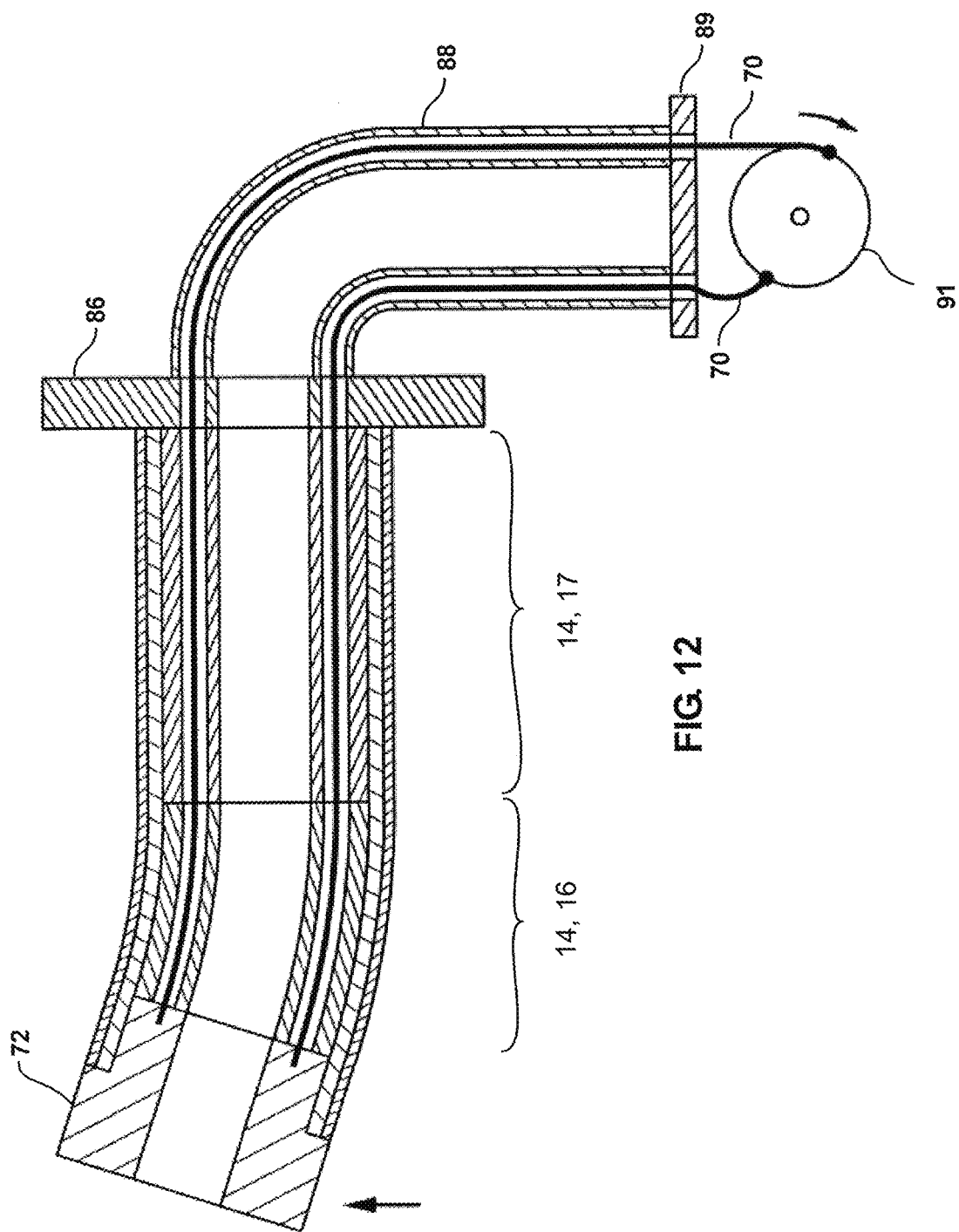
FIG. 12 schematically details the structure of the cylindrical elongated member of FIG. 11A, in a bent position.

In the FIGS. 11A and 12, head 72 represents either a standalone head retained in recess 26, as detailed previously, or alternatively a head in combination with a ring 71 as detailed in relation with FIG. 11B.

FIG. 12 shows the elongated member 14 of FIG. 11A in a bent position, as a result of rocker element 91 having been rotated clockwise. In FIG. 12, the clockwise rotation of rocker 91 causes the rightmost/upper tensioning wire 70 to be pulled out of the hole in stop ribs 89 and out of elongated member 14. According to an embodiment of the present disclosure the difference in durometer of the distal portion 16 and the proximal portion 17 of elongated member 14 is such that pulling the upper tensioning wire 70 out of elongated member 14 bends distal portion 16 upwards (in the figure) along the plane of the figure, as shown by the upwardly turned arrow. It is to be noted that pulling the rightmost/upper tensioning wire 70 with rocker 91 effectively pushes the leftmost/lower tensioning wire 70, and causes it to slack, as illustrated in the figure. According to an embodiment of the disclosure, wire 70 is provided to not break when submitted to such a slack. According to an embodiment of the present disclosure, the material that forms the elongated member 14 does not automatically spring back to center; and the elongated member 14 requires opposite pull-wire tension to steer it back to a straight position.

Figure 13:
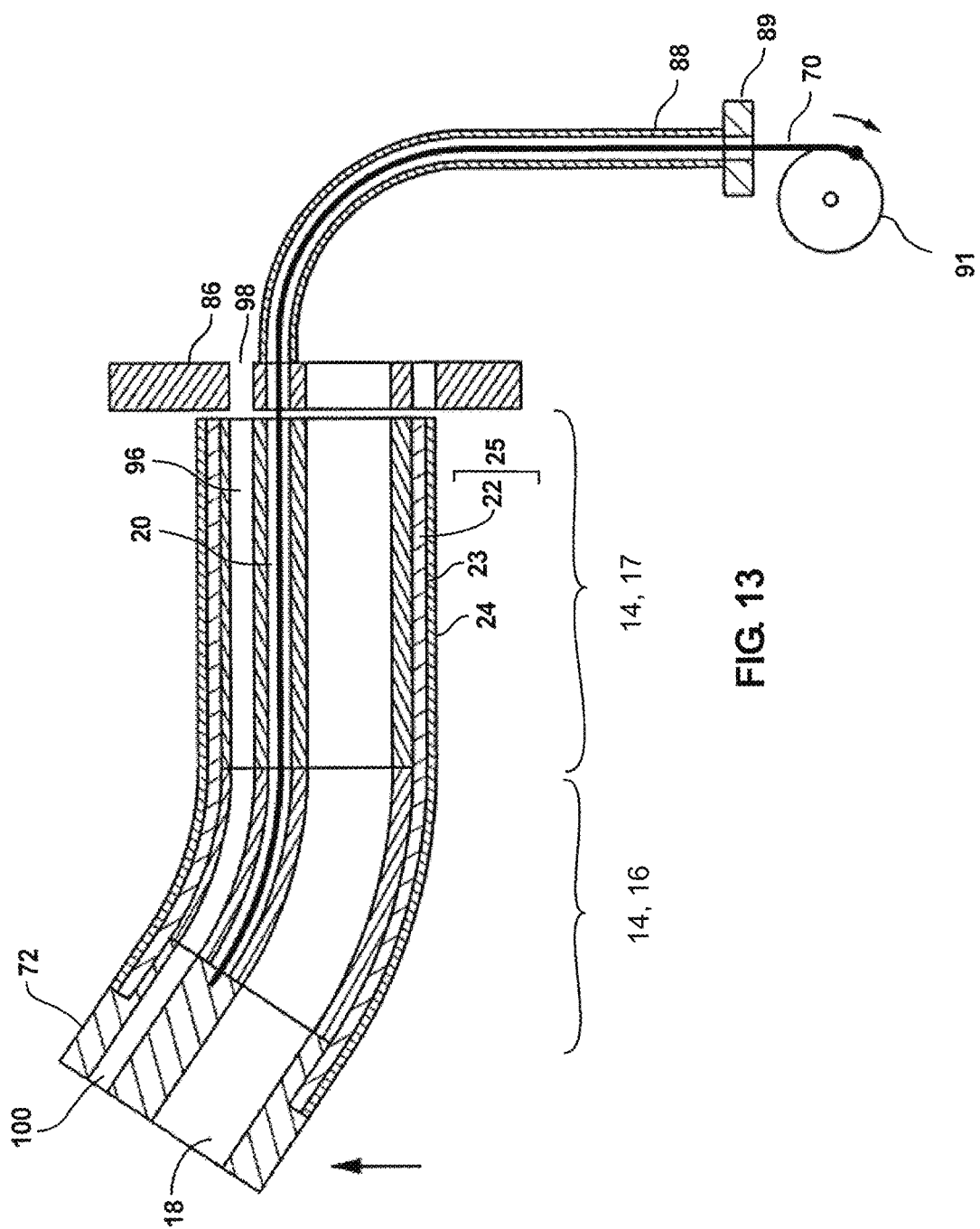
FIG. 13 schematically details the structure of the cylindrical elongated member of a steerable micro-device according to an embodiment of the present disclosure, in a bent position.

FIG. 13 shows schematically the elongated member 14 of an embodiment of the present disclosure identical to the one in FIG. 11A, but having a single tensioning wire 70. FIG. 13 shows elongated member 14 bent upward, in a plane containing both the axis of elongated member 14 and wire 70, by a clockwise rotation of rocker 91. According to an embodiment of the present disclosure, the material that forms the elongated member 14 does automatically spring back toward a straight position when the tension on wire 70 is released. The elongated member 14 of FIG. 13 further comprises an additional lumen 96, which is aligned with an aperture 98 in washer 86 and a lumen 100 in head 72, and which may be used to pass an optical fiber, a fluid or a tool.

Figure 14:
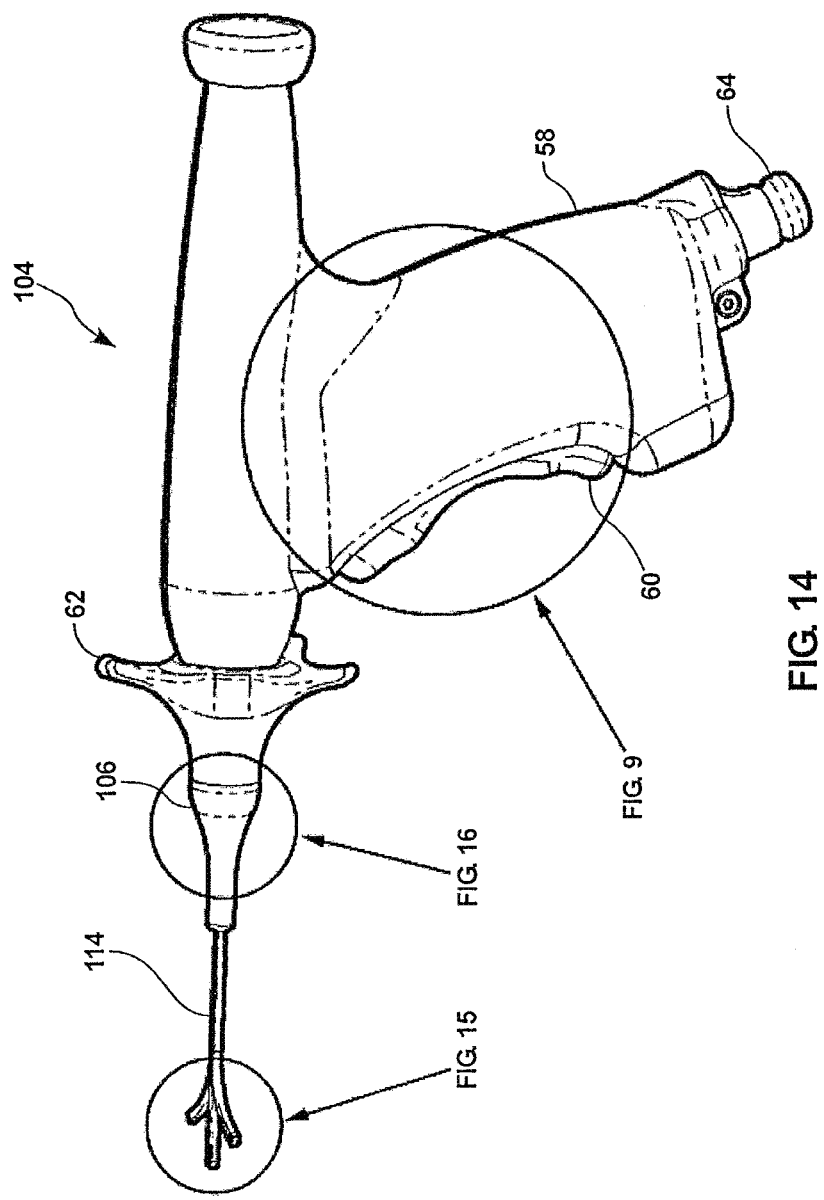
FIG. 14 is an elevation view of a steerable micro-device according to an embodiment of the present disclosure.
Figure 15:
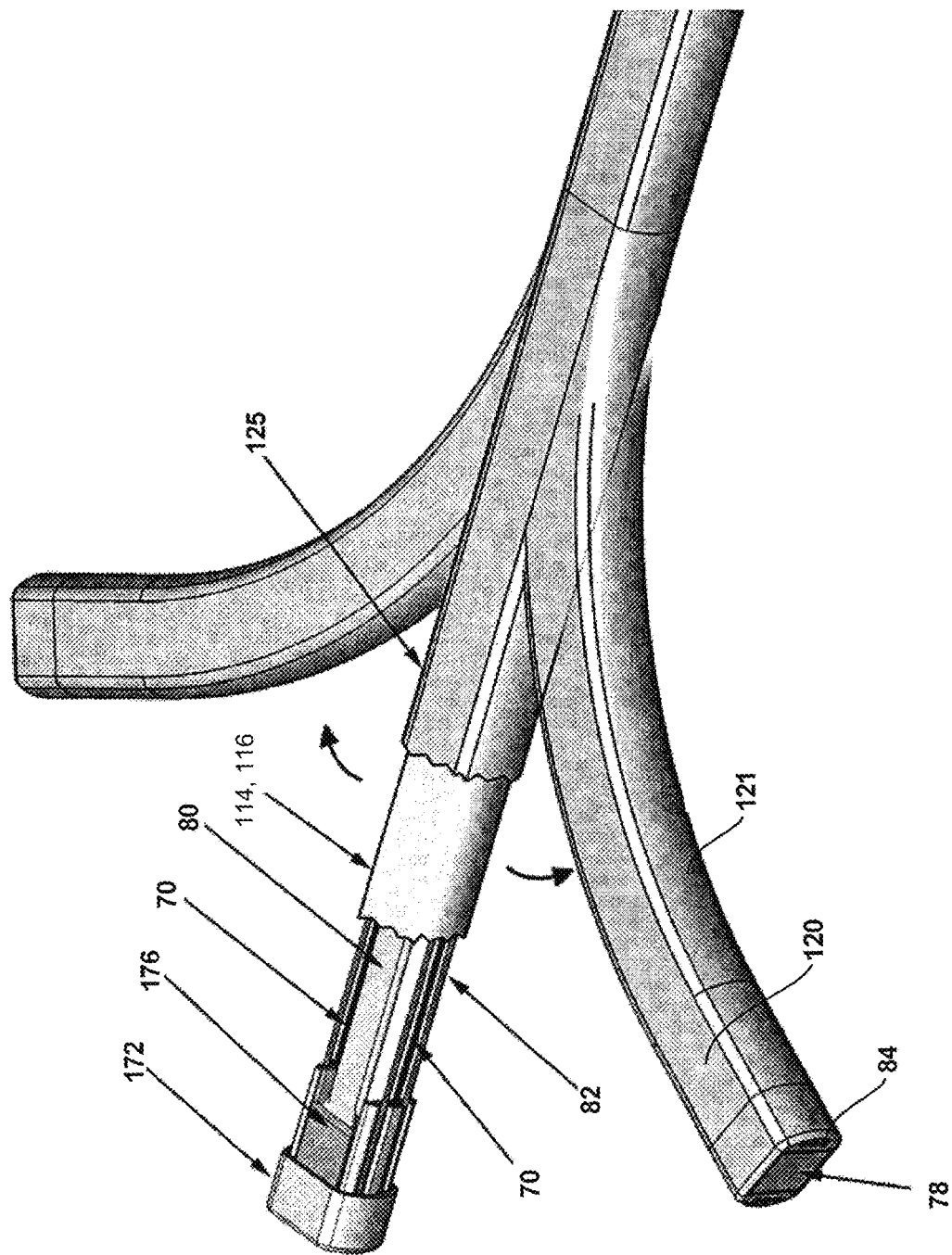
FIG. 15 details the structure of the distal end of the steerable micro-device of FIG. 14 in an unbent position and shows an elevation view of the same distal end in two symmetrical bent positions.

FIG. 14 is an elevation view of a steerable micro-device 104 according to an embodiment of the present disclosure. Micro-device 104 is identical to the micro-device 54 illustrated in FIG. 6, except that it comprises an elongated member 114 that differs from elongated member 14. Elongated member 114 differs from elongated member 14 essentially in that elongated member 14 has a circular cross-section, where elongated member 114 has a flattened cross-section and comprise two parallel flat surfaces, as detailed hereafter. Similar to elongated member 14 which comprises extruded portions 16 and 17 of same cross-section, elongated member 114 comprises extruded portions 116 and 117 of same cross-section. As illustrated in FIG. 15, elongated member 114 can comprise two tensioning wires 70 located in a same plane parallel to its flat surfaces, symmetrically with respect to the axis of elongated member 114, thus allowing to bend the distal portion of elongated member 114 along said plane, toward one tensioning wire or the other.

FIG. 15 shows the distal portion 116 of the sheathed elongated member 114 in an unbent position, with distal parts of extruded distal portion 116 and outer tube 125 removed for clarity of illustration. FIG. 15 also shows the distal portion 116 of sheathed elongated member 114 in two bent positions, in result to the pulling of a proximal end (not shown) of each of the two tensioning wires 70. According to an embodiment of the present disclosure, elongated member 114 comprises two parallel flat surfaces 120 (one shown) joined by convex half-pipe surfaces 121 (one shown). According to an alternative embodiment of the present disclosure (not shown), elongated member 114 has an oval cross-section. According to an embodiment of the present disclosure, elongated member 114 has a non-circular cross section and outer tube 125 has a corresponding cross-section, with the inner dimensions of the cross-section of the lumen of outer tube 125 slightly larger than the outer dimensions of the cross-section of elongated member 114, for example by 0 to 60 micrometer in a direction normal to the outer surface of elongated member 114. According to an embodiment of the present disclosure, similar to outer tube 25 that as detailed previously comprises an extruded torque tube 22 of appropriate cross-section, around which a torque mesh sheath 23 is wound before being wrapped in an outer sheath 24, outer tube 125 is comprised of an extruded torque tube 122 of appropriate cross-section, around which a torque mesh sheath 123 is wound, before being wrapped in an outer sheath 124.

According to an embodiment of the present disclosure, a distal end of the distal portion 116 of sheathed elongated member 114 comprises a head 172. Head 172 is similar to head 72 of for example FIG. 7, except that it has a flattened cross section identical to the cross section of the elongated member 114, and that it comprises less optical fiber lumens 84. Preferably, a proximal portion 176 of the head 172 is provided for fitting in a cavity (not shown) formed by having the outer tube 125 extend beyond the distal end of elongated member 114. Head 172 can be attached to the sheathed elongated member 114 for example by gluing the proximal portion 176 of the head 172 in such cavity. According to an embodiment of the present disclosure, the distal end of both tensioning wires 70 are attached to head 172.

According to an embodiment of the present disclosure, the head 172 comprises a camera 78 that can be identical to the camera used in head 72.

According to an embodiment of the present disclosure, elongated member 114 can comprise additional lumens within which run one or more optical fibers 82, which communicate with lumens 84 in the head 172 to allow outputting light from head 172. FIG. 15 shows an embodiment comprising four optical fibers 82 ending up in two pairs of lumens 84 in the distal surface of head 172.

According to an embodiment of the present disclosure, the larger dimension of the cross-section of sheathed elongated member 114 is lower than 2 millimeter; and preferably lower than 1 millimeter.

Figure 16:
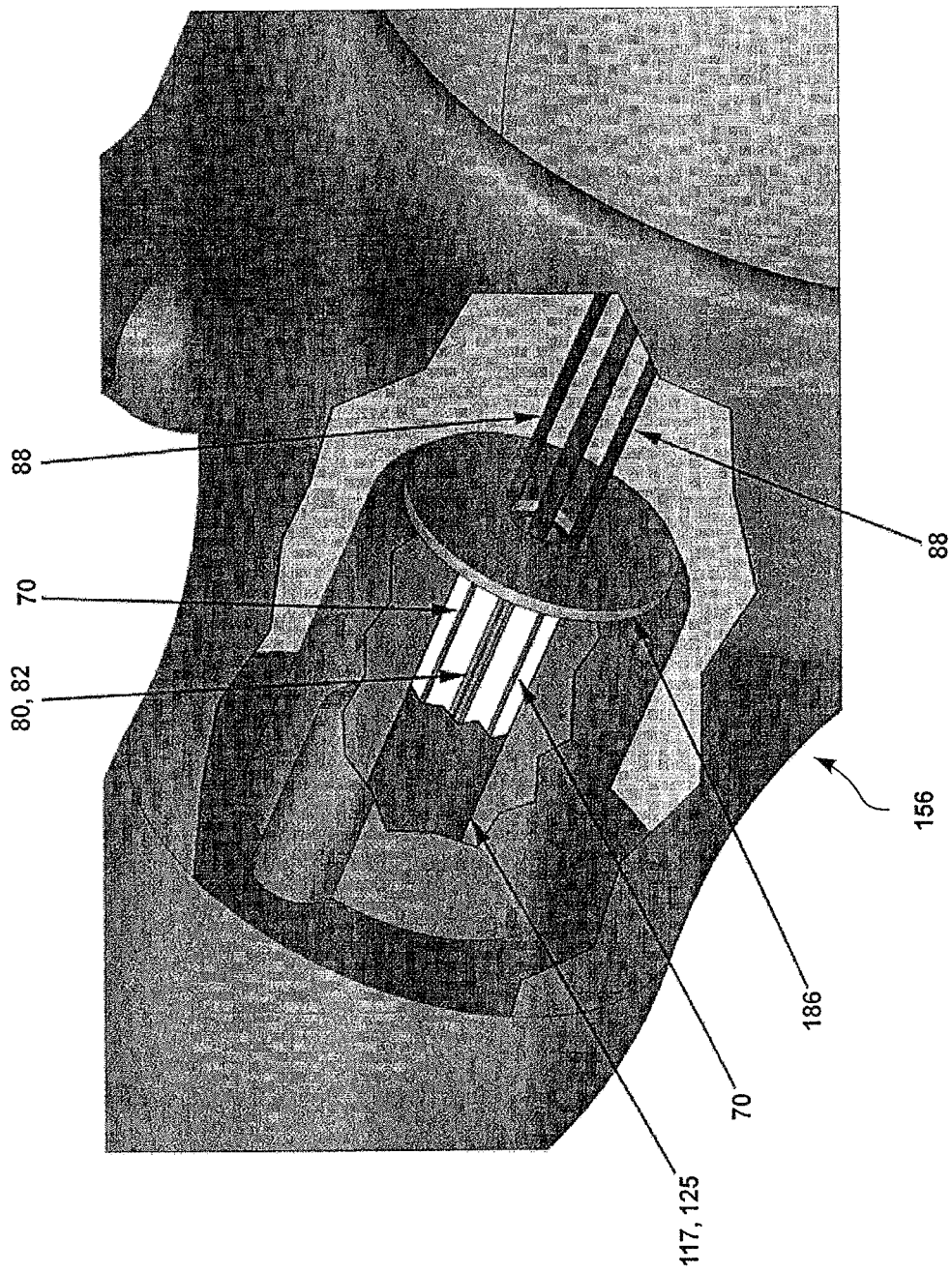
FIG. 16 details the structure of the proximal end of the steerable micro-device of FIG. 14.

FIG. 16 details an exemplary structure of basis 156, to which is attached the proximal end of elongated member 114 as shown in FIGS. 14-15. Basis 156 is essentially identical to basis 56, except that it is provided for being attached to flattened elongated member 114. Further, basis 156 comprises a washer 186 with holes provided for receiving the symmetrically arranged tensioning wires 70. In that respect, the embodiment illustrated in FIGS. 14-16 are similar to the structure schematically illustrated in FIGS. 11A-12.

Figure 17:
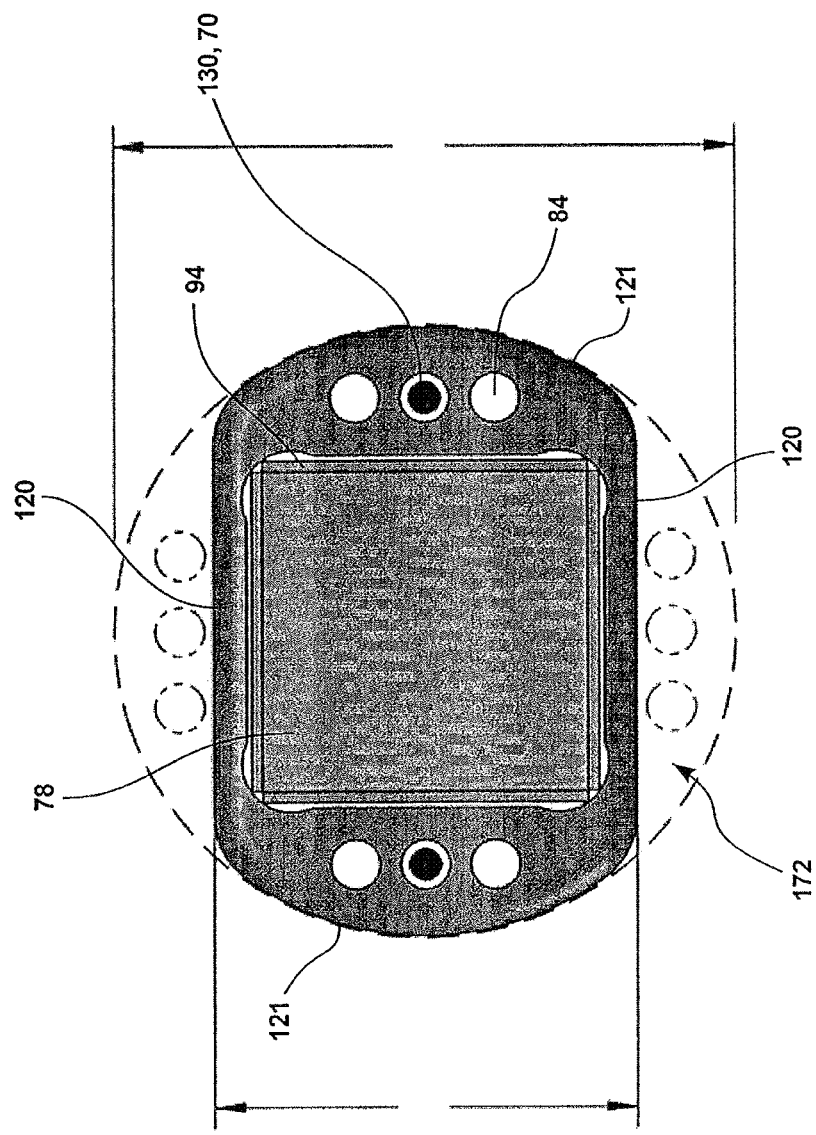
FIG. 17 is a front view of the distal end of the steerable micro-device of FIG. 14.

FIG. 17 is a front view of the distal end of head 172 of FIG. 7, showing the distal surface/window of camera 78, as well as the four lumens 84. According to an embodiment of the present disclosure, the end of each lumen 84 can comprise a microlens for processing the light output by the optical fiber in the lumen 84. FIG. 17 shows that elongated member 114 comprises two parallel flat surfaces 120 joined by convex half-pipe surfaces 121. FIG. 17 also shows the distal ends of two lumens 130, aligned with the lumens 20 of elongated member 114 that comprise the tensioning wires 70. According to an embodiment of the present disclosure, the distal ends of tensioning wires 70 are attached in lumens 130.

Figure 18:
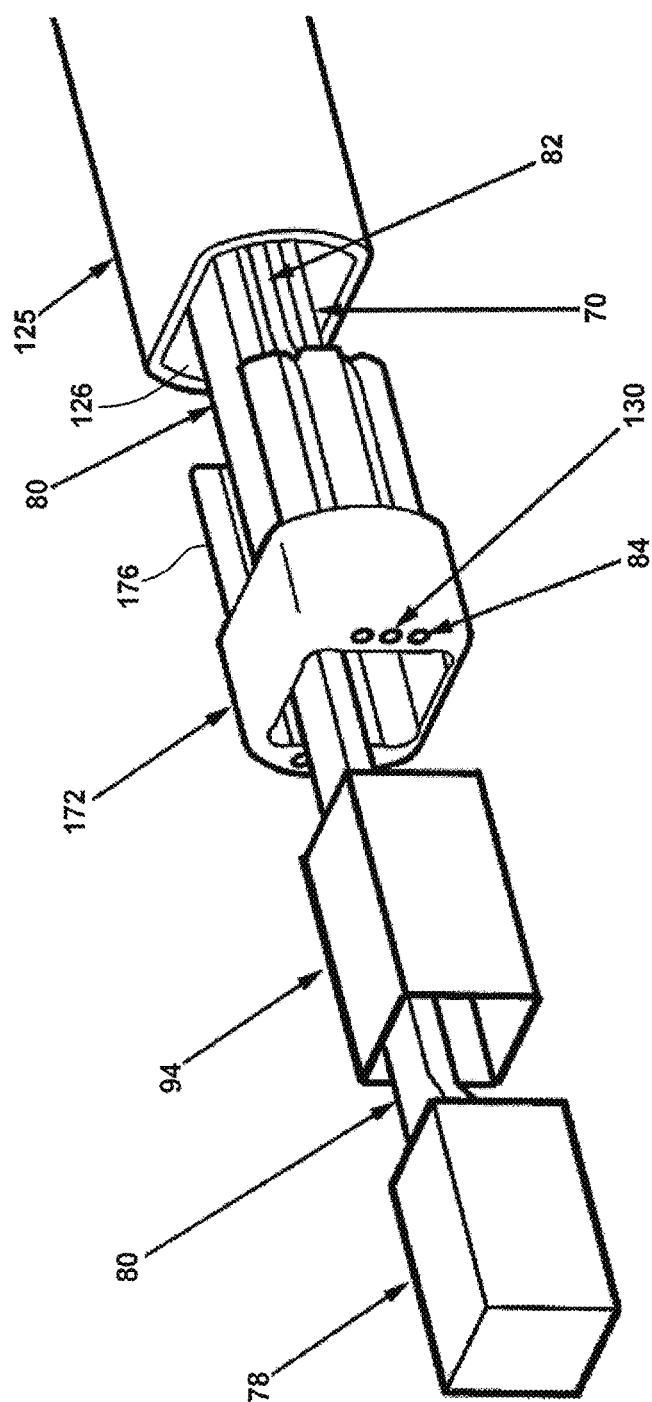
FIG. 18 is an exploded view of the distal end of the steerable micro-device of FIG. 14.
Figure 19:
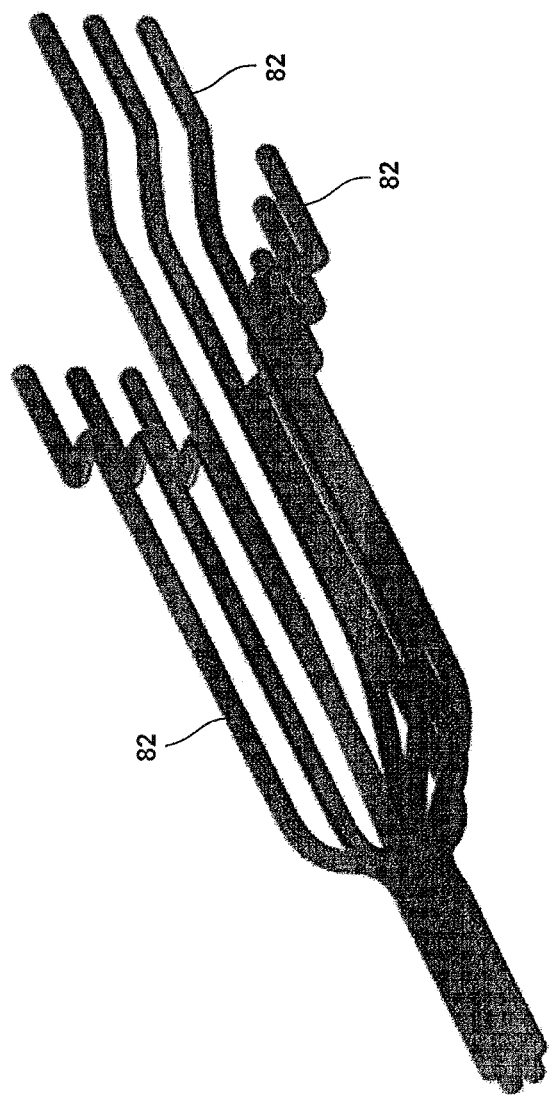
FIG. 19 illustrates a fiber optic bundle used in a steerable micro-device according to an embodiment of the present disclosure.

FIG. 18 is an exploded view of the distal end of the steerable micro-device of FIG. 14. According to an embodiment of the present disclosure, camera 78 fits in a Faraday shielding box 94, which fits in a recess of head 172 that is concentric with the longitudinal axis of head 172. Faraday shielding box can be made of folded sheet metal. Head 172 comprises a narrow proximal portion 176 provided for fitting in a recess 126 formed by having outer tube 125 extend beyond the distal end of elongated member 114 (not shown). The shielded camera cable 80 along with tensioning wires 70 and optical fibers 82, can each run through dedicated lumens in elongated member 114. Alternatively, optical fibers 82 can run as a bundle in a single lumen of elongated member 114, for example together with cable 80 in a central lumen of elongated member 114. In such an embodiment, the optical fiber bundle can separate into individual fibers 82 just at the distal end of elongated member 114, as illustrated in FIG. 19.

A micro-imaging scope or micro endoscope 54 or 154 according to an embodiment of the present disclosure has been designed for medical inspection inside the body (for human or veterinary use), for steering with one or two wires, and to be relatively small and relatively inexpensive. Because such device is commonly used to view a cavity inside the body which has no available light, a device according to embodiment of the present disclosure comprises a lighting component that uses fiber optic to deliver the illumination at the distal end of the elongated member 14 or 114, which can also comprise an imaging sensor or camera 78. According to an embodiment such as shown in FIGS. 15-18, four optical fibers 82 can be used, one for each of the four sides of the imaging sensor 78 at the distal end of the elongated member 114. In addition, a micro-device according to an embodiment of the present disclosure is designed to use relatively inexpensive parts such that it is disposable after use in a procedure.

An embodiment of the present disclosure relates to a highly integrated system featuring illumination, imaging and steering based on material properties of each individual component which allows performing the functionality of these integrated features together in a micro-scale system.

According to an embodiment of the present disclosure the entire system is completely steerable with at least one pull wire 70. However, embodiments of the present disclosure can also comprise two pull wires or tensioning wires 70. Two wires 70 on a same side of the elongated member as shown in FIG. 7 allow for steering in one direction only. Systems with two wires on opposing sides of the elongated member as shown in FIG. 15 allow for steering in opposite directions.

According to an embodiment of the present disclosure, the length of softer (25d) material used on the distal end of the elongated member is going to allow for more compression (the amount of bend) for that end, and the ratio of soft (25d) to hard (75d) determines that amount of bend.

According to an embodiment of the present disclosure, the system accomplishes several things, rotation, up & down/side-to-side motion, depending on orientation.

According to an embodiment of the present disclosure, each pull-wire 70 can have push-tubing 88 inside of the handle 58 or housing, where the push-tubing 88 allows for opposing force to push against and this design gives the tension required to make the pull-wire 70 move longitudinally without bending inside the handle end. In addition a twist (rotation) of the proximal end of the elongated member can be produced around the strain-relief and this will produce rotation on the distal end of the catheter/endoscope without affecting tension on the push-tubing in the handle.

According to an embodiment of the present disclosure, in embodiments using a two pull-wire system with the pull-wires 70 on opposing sides, the trigger handle or lever 60 can apply stress on one pull-wire 70, which results in a slack in the opposite pull-wire 70, and the stress on the pull-wire will compress and bend the distal end of the elongated member in the direction of the pull.

According to an embodiment of the present disclosure, the outer tube 25/125 is designed to hold the rotation and still allow for bending of distal end due to steering. According to an embodiment of the present disclosure, the outer tube 25/125 further protects the wire 70 from breaking through the relatively softer plastic or material of the elongated member 14/114.

An embodiment of the present disclosure relates to a micro endoscope with highly integrated function of imaging, illumination, steering or navigation in low cost, disposable, flexible plastic, catheter/endoscope.

A micro-endoscope according to embodiments of the present disclosure has the combined functions of flexibility, imaging and steering as typically implemented in larger size endoscopes. Combining these features in low cost micro scale endoscope demanded innovative ways to combine functions, so each element contributes multiple functions to cause miniaturization and cost reduction. A micro-endoscope according to embodiments of the present disclosure uses plastic extrusion that provides embodiment of the catheter/endoscope containing imaging and illumination, but also participates in steering mechanism so it can be reduced in size.

Micro multi-lumen extrusion can be made for example using flexible plastic. Subsequently or alternatively, several relief cuts can be made in the distal section of the extrusion making this section more flexible then the rest of the extrusion. According to embodiments of the present disclosure, placing pull wire 70 in the side of micro lumen along the side of the extrusion allows compressing the length of the extrusion, causing it to bend the section that is more flexible, for example the distal portion of the elongated member. This feature combined with rotation of the elongated member/extrusion allows for 360 degree navigation. According to an embodiment of the disclosure, a center lumen in the extrusion can receive an imaging camera or an imaging fiber bundle. According to an embodiment of the disclosure, the remaining space around center lumen can be used to place illumination fiber. This way, the presence of a steering mechanism is not contributing to the overall size of the endoscope, because it occupies essentially a portion of the same space that is already taken by the illumination fibers.

According to an embodiment of the disclosure, the steerable micro-device can use multiple wires to produce more sophisticated steering control.

As detailed above, according to an embodiment of the disclosure, the difference in flexibility of extrusion can be accomplished by introduction of an extrusion section with the same cross-section but made of softer, more compressible plastic. According to an embodiment of the disclosure, another way to accomplish the same effect is to make a single micro lumen extrusion or elongated member from softer plastic, and introduce a harder sheath or tube into a lumen of the elongated member, such as the center lumen in order to increase the durometer of the proximal section of the elongated member.

As detailed above, embodiments of a steerable micro-device according to the present the disclosure comprise a plurality of lumens, formed by extrusion of the elongated member, an imaging camera or an imaging fiber bundle arranged to transmit a picture of what is in front of the distal end of the elongated member, at least one illumination fiber running through a lumen, at least one pull wire or tensioning wire running through a lumen, a distal head that secures the camera or the distal end of the fiber bundle as well as the distal end of the illumination fiber and the distal end of the pull wire, a torque braid sheath, a handle housing and a connector for coupling the housing to at least an external monitor.

As detailed above, according to embodiments of the disclosure, when the pull wire 70 is pulled on the proximal end, the softer section of the extrusion compresses first before the harder section and because the pull wire is not in the center of the extrusion, but instead in the micro lumen on the side of the extrusion, it results in the softer section to compress unevenly and bend. The amount of the bend is directly proportional to the force applied to the wire, the ratio of the plastic hardness between soft and hard sections of the extrusion and the distance of the pull wire from the center of the extrusion/elongated member. Combined with the rotation of the elongated member, such embodiment allows a 360° navigation of the distal end of the elongated member. As detailed above, the torque braid sheath applied to the extrusion directly under the outside jacket of the extrusion provides the rotational response of the extrusion to torque forces without compromising flexibility of the extrusion. A micro-endoscope according to embodiments of the present disclosure can be used for diagnosis in micro invasive procedures in many cases eliminating a need for costly MRI's. The same micro-endoscopes can be equipped with a tool to perform biopsies in micro-invasive procedures in doctor's office requiring only local anesthetic in contrast to surgery done in the hospital under general anesthesia.

A device according to the present disclosure, having a camera and an optic fiber to transmit light, is particularly suitable as a micro-endoscope in the medical domain, but it can also be used in the automotive domain or the home improvement domain to look into hard-to-reach locations.

The present disclosure also relates to a method of manufacturing a steerable micro-device such as a micro-endoscope. The method may comprise extruding the proximal portion of the elongated member in a first material; extruding the distal portion of the elongated member in a second material; sliding the distal and proximal portions on an assembly support passing through the lumens so that the distal and proximal portions are properly aligned, and attaching the distal and proximal portions together. The elongated member is then removed from the assembly support and the tensioning wire or wires, and eventually the fiber illumination optical fiber or fibers and the camera wires are introduced in the lumens. The head of the elongated member is then attached to the elongated member. The head can be attached to the tensioning wire or wires, the fiber illumination optical fiber or fibers and the camera wires before or after they are introduced in the lumens.

After the head is attached to the elongated member, the torque mesh sheath is attached to, or formed around, the elongated member, then covered by the external sheath. The elongated member can be attached to the rotatable base before or after the torque mesh sheath is attached to, or formed around, the elongated member. The base can comprise a stop washer with holes letting through the tensioning wires, the optical fibers and the camera cable or optical fiber bundle. The proximal end of the torque mesh sheath is attached to the rotatable base.

Alternatively to forming the distal and proximal portions in two different materials, the proximal portion and the distal portion of the elongated member can be made out of a single material. A sheath can then be inserted in at least one lumen of the elongated member along the proximal portion of the elongated number to increase the durometer of the proximal portion with respect to the durometer of the distal portion.

Alternatively, the proximal portion and the distal portion of the elongated member can be made out of a single material; and matter can be removed from the elongated member in the distal portion to lower the durometer of the distal portion with respect to the durometer of the proximal portion. According to an embodiment of the present disclosure, matter is removed from the elongated member in the distal portion by forming at least one cut in a plane that does not comprise the axis of the elongated member. According to an embodiment of the present disclosure, matter is removed from the elongated member in the distal portion by forming at least one bore along an axis that differs from the axis of the elongated member. Alternatively, at least one lumen of the distal portion can be enlarged by removing material along an axis parallel to the axis of the elongated member to reduce the durometer of the distal portion. According to an embodiment of the present disclosure, matter is removed from the elongated member in the distal portion by treating chemically the distal portion.

As detailed above, embodiments of present disclosure relate to a steerable micro-device such as a micro-endoscope, having an elongated member with a non circular cross section. Components of an imaging endoscope typically comprise an imaging sensor and illumination. More sophisticated scopes would have one or more working channels providing space for delivery of tools, or therapy and stirring mechanism. Micro endoscopes according to embodiments of the present disclosure have the same components, but they have to be smaller. Space limitation imposed by the small dimension of the scope has profound consequences on cost, function and application of the scope. Limits in miniaturization technology of the imaging methods, optical components and general manufacturing techniques set the boundary of the overall scope size on one hand. On the other hand, micro invasive devises answer to rapidly growing need for smaller devices reaching smaller physiology delivering diagnosis and treatment, minimizing in the same time, procedure cost and trauma to the patient.

According to embodiments of the present disclosure, the imaging component is a driving element of the scope size that is typically surrounded by donut circle of illumination components producing uniform and symmetrical cylinder. According to other embodiments of the present disclosure, one way to minimize scope size is to position the illumination components only on two sides of the imaging sensor instead of the above-described radial distribution. This leads to the oval shape of the scope. The critical benefit of the oval scope is as much as 30% reduction of the profile size in one direction. As the direct result of this shape, scope can be introduced in to much smaller physiology without any compromise of the image quality or function. As a matter of fact, the oval or flattened shape of the scope results in superior torque and added stability.

An imaging scope according to an embodiment of the present disclosure has been designed as small and flat as possible for medical inspection inside the body (for human or veterinary use) with the capability of steering. Because the scope is commonly used to view a cavity inside the body which has no available light, a lighting component was added using fiber optic cable to deliver the illumination at the distal end on the left and right sides of the imaging sensor. In addition, this scope is designed to use relatively inexpensive parts such that it is disposable after use in a procedure.

Typical construction of the endoscope calls for imaging elements illumination and steering mechanism. The traditional approach is to distribute illumination regularly around the imaging component. Steering mechanism is usually placed around the illumination or it shares the orbit with illumination. This results typically in the circular shape of the endoscope. To minimize the size of the scope, an embodiment of the present disclosure clusters all the fibers and the steering mechanism wires in opposing sides of the center that is occupied by an imaging system. The imaging system becomes the driving component of the size of the entire scope. The benefit resulting from the flat shape of the micro endoscope is significant reduction in size in one direction (height) that allows for easier access in the tide physiology of small spaces without compromising any of the functionality of the scope such as steering, image quality, or illumination.

Common methods of illumination rely on existing light sources like halogen, ark lamps, plasma and more recently LED and laser. A technical difficulty in illumination in a micro-endoscope according to the present disclosure is the lack of space to position light source in a distal end of the scope. Use of the light transmitting fibers is a common solution, but the size of the light bundle is limited by the method of coupling light in to the bundle. A main objective of coupling white light to the bundle gets to be increasingly difficult with scaling down the size of the bundle. This is caused by the non-coherent nature of white light and the physical size of the element providing luminescence that does not lend itself to focusing in to the very small spot required for coupling in to the small fiber. According to an embodiment of the present disclosure, a LED is a preferred light source because of its small size, low price and efficiency in producing lot of light. A problem however lies in the way that a LED can produce white light. A LED chip itself is not capable of emitting light in the broad spectrum covering the white light, or a visible range of the spectrum 420 nm-to 720 nm. Accordingly, an embodiment of the present disclosure uses fluorescent phosphor to convert a narrow (e.g. 15 nm) band illumination typically between 350 nm to 470 nm, to the desired broad spectrum. According to an embodiment of the present disclosure, the fluorescent phosphor is not arranged in the LED itself, but in the distal end of the fiber. This accomplishes several things:

1. No phosphor on LED, which allows to bring up coupling efficiency even by direct contact of the fiber with the LED chip;

2. No need for high NA fiber, a device according to such an embodiment of the present disclosure can use standard, low cost step index multi-mode fibers;

3. Placing phosphor on the tip of the fiber creates a scattered, broad spectrum illumination at the distal end of the fiber and thus of the elongated member;

4. The dispersive pattern of illumination caused by phosphor creates a wide field, uniform illumination eliminating the need for additional optics. This is critical to take full advantage of the imaging broad field of view otherwise not matched by low NA fiber illumination;

5. Eliminating the need for expensive optics in coupling assembly minimizes the overall size of the coupling assembly and lends itself to be placed in the handle of the scope (with adequate heat dissipation), lowering cost, simplifying assembly and connection to the control unit; and 6. Efficiency of the coupling lowers operating temperature and extends the LED life.

The reference US 2012/0018082 describes an illumination device that includes an optical fiber holder configured to hold an optical fiber, a phosphor holder configured to hold a phosphor that faces the optical fiber holder, and a bonding material configured to intervene between the optical fiber holder and the phosphor holder to bond them. The illumination device includes adjustment guide members configured to intervene between the optical fiber holder and the phosphor holder, relatively positionally adjust the optical fiber holder and the phosphor holder so as to arrange an optical axis of the optical fiber and an optical axis of the phosphor on one line, and configured to prevent the optical fiber holder and the phosphor holder from tilting when the bonding material is cured.

The Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the step(s) of . . . ."

All elements, parts and steps described herein are preferably included. It is to be understood that any of these elements, parts and steps may be replaced by other elements, parts and steps or deleted altogether as will be obvious to those skilled in the art.

Overall, the present disclosure relates to the following concepts:

Concept 1. A steerable micro-device comprising a cylindrical elongated member having a distal end and a proximal end, the elongated member comprising at least a first lumen, a tensioning wire running in the first lumen, a distal end of the tensioning wire being attached at the distal end of the elongated member and a proximal end of the tensioning wire exiting the first lumen at the proximal end of the elongated member; the elongated member having a proximal portion extending from the proximal end toward the distal end of the elongated member and a distal portion extending from the distal end to the proximal portion of the elongated member, the proximal portion having a first durometer and the distal portion having a second durometer, lower than the first durometer; the first lumen being arranged such that the distal portion of the elongated body bends when the proximal end of the tensioning wire is pulled.

Concept 2. The steerable micro-device of concept 1, wherein the elongated member is held in an outer tube comprising:

a torque tube having an axial lumen with an inner diameter equal to, or slightly larger than, the outer diameter of the elongated member; and a mesh-sheath wound around the torque tube.

Concept 3. The steerable micro-device of concept 2, wherein the torque mesh-sheath is covered by an outer sheath.

Concept 4. The steerable micro-device of concept 1 to 3, wherein the first durometer is chosen such that the proximal portion is flexible enough to be inserted in a desired body cavity without damaging the cavity, and the second durometer is chosen such that when the tensioning wire is pulled, the distal portion bends.

Concept 5. The steerable micro-device of concept 1 to 4, wherein the second durometer is chosen such that when the tensioning wire is relaxed after having been pulled, the distal portion tends to return to an unbent shape.

Concept 6. The steerable micro-device of concept 1 to 5, wherein the elongated member comprises a second lumen; an optical fiber arranged in the second lumen having a proximal end capable of receiving light from a source of light and a distal end capable of emitting light received at the proximal end from the distal end.

Concept 7. The steerable micro-device of concept 6, wherein the proximal end of the optical fiber is coupled with a connector for interfacing with a source of light.

Concept 8. The steerable micro-device of concept 6, wherein the elongated member comprises at least two second lumens arranged on both sides of the first lumen along a diameter around the axis of the elongated member.

Concept 9. The steerable micro-device of concept 1 to 8, wherein the elongated member comprises a third lumen and the distal end of the elongated member comprises a camera, at least a first wire of the camera running through the third lumen.

Concept 10. The steerable micro-device of concept 1 to 9, wherein the distal end of the elongated member is in contact with the proximal end of a ring structure; the ring structure forming a loop path through which the tensioning wire runs, the loop path being provided for preventing the tensioning wire from slipping, whereby a pull on the tensioning wire exerts pressure on the distal end of the elongated member around said tensioning wire.

Concept 11. The steerable micro-device of concept 9 or 10, wherein a second wire of the camera runs through the third lumen.

Concept 12. The steerable micro-device of concept 9 to 11, wherein the proximal ends of the wires of the camera are coupled to a connector for interfacing with an imaging device.

Concept 13. The steerable micro-device of concept 9 to 12, wherein the camera is aligned along the axis of the elongated member.

Concept 14. The steerable micro-device of concept 9 to 13, wherein the distal end of the distal portion comprises a head made in a material different from the material of the elongated member, a distal portion of the head having the same cross section as the elongated member with the torque mesh sheath and the outer sheath or jacket.

Concept 15. The steerable micro-device of concept 14, wherein a proximal portion of the head is inserted in a cavity formed at the distal end of the elongated member.

Concept 16. The steerable micro-device of concept 14 to 15, wherein the distal end of the tensioning wire is attached to the head.

Concept 17. The steerable micro-device of concept 14 to 16, wherein the camera is held in the head.

Concept 18. The steerable micro-device of concept 14 to 17, wherein the head comprises at least one lumen through which passes the distal end of the optical fiber.

Concept 19. The steerable micro-device of concept 1 to 18, wherein the elongated member comprises a fourth lumen enabling to pass a fluid from the proximal end to the distal end of the elongated member.

Concept 20. The steerable micro-device of concept 1 to 19, wherein the elongated member has a circular cross-section with a diameter lower than 2 millimeter.

Concept 21. The steerable micro-device of concept 20, wherein the elongated member has a diameter lower than 1 millimeter.

Concept 22. The steerable micro-device of concept 1 to 19, wherein the elongated member has a non circular cross-section with a maximum dimension lower than 2 millimeter.

Concept 23. The steerable micro-device of concept 22, wherein the elongated member has a cross-section with a maximum dimension lower than 1 millimeter.

Concept 24. The steerable micro-device of concept 1 to 23, wherein the tensioning wire has a diameter of 0.15 millimeter or less.

Concept 25. The steerable micro-device of concept 1 to 24, wherein the elongated member comprises two first lumen containing each a tensioning wire, the distal ends of the tensioning wires in the two first lumens being joined together.

Concept 26. The steerable micro-device of concept 1 to 25, wherein the tensioning wire is coated with a lubricant and is in direct contact with the inner walls of the first lumen.

Concept 27. The steerable micro-device of concept 1 to 26, wherein the elongated member and the torque tube are each fabricated separately by a continuous process.

Concept 28. The steerable micro-device of concept 1 to 27, wherein the proximal end of the elongated member is attached to a base that is rotatable with respect to a proximal housing around an axis of the proximal end of the elongated member.

Concept 29. The steerable micro-device of concept 28, wherein the base is rotatable manually.

Concept 30. The steerable micro-device of concept 28 to 29, wherein the base comprises a lock for controllably locking the base rotated along a desired angle.

Concept 31. The steerable micro-device of concept 28 to 30, wherein the housing comprises a lever for controllably pulling on the proximal end of the tensioning wire.

Concept 32. The steerable micro-device of concept 31, wherein the lever comprises a lock for locking the tensioning wire pulled along a desired length.

Concept 33. The steerable micro-device of concept 31 to 32, wherein the tensioning wire passes through a flexible sheath that is not compressible axially between the base and the lever.

Concept 34. The steerable micro-device of concept 31 to 33, wherein the tensioning wire is coupled to the lever using cogwheels or gears.

Concept 35. The steerable micro-device of concept 34, wherein the ratio between the cogwheels or gears can be changed to adjust the sensitivity of the lever.

Concept 36. The steerable micro-device of concept 31 to 35, wherein the housing is shaped for being held in one hand, such that the lever can be actuated by tightening the grip of the hand and the base can be rotated by actuation of a knob with the thumb of the hand.

Concept 37. The steerable micro-device of concept 31 to 36, wherein the elongated member comprises two first lumen containing each one tensioning wire, the two first lumens being arranged on diametrically opposed sides of the axis of the elongated member.

Concept 38. The steerable micro-device of concept 37, wherein the lever of the housing is arranged such that pressing one end of the lever pulls on the proximal end of the tensioning wire in one of the first lumens and pressing another end of the lever pulls on the proximal end of the tensioning wire in the other of the first lumens.

Concept 39. The steerable micro-device of concept 1 to 38, wherein the elongated member has a circular cross section.

Concept 40. The steerable micro-device of concept 1 to 38, wherein the elongated member has an elliptic cross section.

Concept 41. The steerable micro-device of concept 1 to 38, wherein the elongated member has a cross section comprising two half circles joined by straight lines.

Concept 42. The steerable micro-device of concept 1 to 41, wherein the proximal portion and the distal portion of the elongated member are extruded out of two different materials and are assembled together after extrusion.

Concept 43. The steerable micro-device of concept 1 to 41, wherein the proximal portion and the distal portion of the elongated member are made out of a single material; a sheath being inserted in at least one lumen of the elongated member along the proximal portion of the elongated number to increase the durometer of the proximal portion with respect to the durometer of the distal portion.

Concept 44. The steerable micro-device of concept 1 to 41, wherein the proximal portion and the distal portion of the elongated member are made out of a single material; and matter is removed from the elongated member in the distal portion to lower the durometer of the distal portion with respect to the durometer of the proximal portion.

Concept 45. The steerable micro-device of concept 44, wherein matter is removed from the elongated member in the distal portion by forming at least one cut in a plane that does not comprise the axis of the elongated member.

Concept 46. The steerable micro-device of concept 44, wherein matter is removed from the elongated member in the distal portion by forming at least one bore along an axis that differs from the axis of the elongated member.

Concept 47. The steerable micro-device of concept 44, wherein matter is removed from the elongated member in the distal portion by treating chemically the distal portion.

What is claimed is:

1. A steerable micro-device comprising an elongated member that is cylindrical and that has a distal end and a proximal end, the elongated member comprising at least a first lumen, a tensioning wire running in the first lumen, a distal end of the tensioning wire being attached at the distal end of the elongated member and a proximal end of the tensioning wire exiting the first lumen at the proximal end of the elongated member;

the elongated member having a proximal portion extending from the proximal end toward the distal end of the elongated member and a distal portion extending from the distal end to the proximal portion of the elongated member, the proximal portion having a first durometer and the distal portion having a second durometer, lower than the first durometer;

the first lumen being arranged such that the distal portion of the elongated member bends when the proximal end of the tensioning wire is pulled;

wherein the elongated member is held in an outer tube comprising:

a torque tube having an axial lumen with an inner diameter that is 0 to 60 micron larger than the outer diameter of the elongated member; and a mesh-sheath wound around the torque tube;

said proximal portion of the elongated member being made of a resilient material; and said proximal portion of the elongated member having been slid inside the axial lumen of the torque tube.

2. The steerable micro-device of claim 1, wherein the torque mesh-sheath is covered by an outer sheath.

3. The steerable micro-device of claim 1, wherein the elongated member comprises a second lumen; an optical fiber arranged in the second lumen having a proximal end capable of receiving light from a source of light and a distal end capable of emitting light received at the proximal end from the distal end.

4. The steerable micro-device of claim 1, wherein the elongated member comprises a third lumen and the distal end of the elongated member comprises a camera, at least a first wire of the camera running through the third lumen.

5. The steerable micro-device of claim 1, wherein the distal end of the elongated member is in contact with the proximal end of a ring structure; the ring structure forming a loop path through which the tensioning wire runs, the loop path being provided for preventing the tensioning wire from slipping, whereby a pull on the tensioning wire exerts pressure on the distal end of the elongated member around said tensioning wire.

6. The steerable micro-device of claim 2, wherein the distal end of the distal portion comprises a head made in a material different from the material of the elongated member, the head having a proximal portion in contact with the distal end of the elongated member and a distal portion extending from the proximal portion along an axis of the elongated member, said distal portion of the head having the same cross section as the elongated member with the torque tube, the torque mesh sheath and the outer sheath.

7. The steerable micro-device of claim 6, wherein said proximal portion of the head is inserted in a cavity formed at the distal end of the elongated member.

8. The steerable micro-device of claim 7, wherein the distal end of the tensioning wire is attached to the head.

9. The steerable micro-device of claim 6, wherein a camera is held in the head.

10. The steerable micro-device of claim 1, wherein the elongated member comprises a fourth lumen enabling to pass a fluid from the proximal end to the distal end of the elongated member.

11. The steerable micro-device of claim 1, wherein the elongated member has a non circular cross-section with a maximum dimension lower than 2 millimeter.

12. The steerable micro-device of claim 1, wherein the elongated member comprises two first lumen containing each a tensioning wire, the distal ends of the tensioning wires in the two first lumens being joined together.

13. The steerable micro-device of claim 1, wherein the elongated member and the torque tube are each fabricated separately by a continuous process.

14. The steerable micro-device of claim 1, wherein the proximal end of the elongated member is attached to a base that is rotatable with respect to a proximal housing around an axis of the proximal end of the elongated member.

15. The steerable micro-device of claim 14, wherein the elongated member comprises two first lumen containing each one tensioning wire, the two first lumens being arranged on diametrically opposed sides of the axis of the elongated member.

16. The steerable micro-device of claim 15, wherein said proximal housing comprises a lever arranged such that pressing one end of the lever pulls on the proximal end of the tensioning wire in one of the first lumens and pressing another end of the lever pulls on the proximal end of the tensioning wire in the other of the first lumens.

17. The steerable micro-device of claim 1, wherein the proximal portion and the distal portion of the elongated member are extruded out of two different materials and are assembled together after extrusion.

18. The steerable micro-device of claim 1, wherein the proximal portion and the distal portion of the elongated member are made out of a single material; a rigidifying sheath being inserted in at least one lumen of the elongated member along the proximal portion of the elongated number to increase the durometer of the proximal portion with respect to the durometer of the distal portion.

19. The steerable micro-device of claim 1, wherein the proximal portion and the distal portion of the elongated member are made out of a single material; and matter is removed from the elongated member in the distal portion to lower the durometer of the distal portion with respect to the durometer of the proximal portion.

\* \* \* \* \*